(12) United States Patent
Dalby et al.

(10) Patent No.: US 11,209,349 B2
(45) Date of Patent: Dec. 28, 2021

(54) OPTICAL FLUID ANALYZER

(71) Applicant: Pietro Fiorentini (USA), Inc., Wheeling, WV (US)

(72) Inventors: David Dalby, Suffolk (GB); Gordon Lamb, Cambs (GB); Michael Hazell, Cambridge (GB); Paul Ryder, Cambridge (GB); Robert Jones, Cambridge (GB); Margaret Waid, Medicine Park, OK (US); Michael Yuratich, Hamble (GB)

( * ) Notice: Subject to any disclaimer, the term of this patent is extended or adjusted under 35 U.S.C. 154(b) by 337 days.

(21) Appl. No.: 16/487,869

(22) PCT Filed: Feb. 22, 2018

(86) PCT No.: PCT/US2018/019080
§ 371 (c)(1),
(2) Date: Aug. 22, 2019

(87) PCT Pub. No.: WO2018/156673
PCT Pub. Date: Aug. 30, 2018

(65) Prior Publication Data
US 2020/0011787 A1 Jan. 9, 2020

Related U.S. Application Data

(60) Provisional application No. 62/463,357, filed on Feb. 24, 2017.

(51) Int. Cl.
*G01N 21/64* (2006.01)
*G01N 21/27* (2006.01)
(Continued)

(52) U.S. Cl.
CPC ......... *G01N 21/276* (2013.01); *E21B 49/081* (2013.01); *E21B 49/10* (2013.01);
(Continued)

(58) Field of Classification Search
CPC ...... E21B 49/081; E21B 49/10; G01J 3/0218; G01J 3/0297; G01J 3/10; G01J 3/12; G01J 3/14; G01J 3/42; G01J 3/4406; G01J 2003/1213; G01J 2003/1221; G01J 2003/1234; G01J 2003/1282; G01J 2003/2869; G01N 21/05; G01N 21/276; G01N 21/359; G01N 21/43; G01N 21/552; G01N 21/645; G01N 33/2823; G01N 2021/1734; G01N 2021/6471
See application file for complete search history.

(56) References Cited

U.S. PATENT DOCUMENTS

| | | | | |
|---|---|---|---|---|
| 5,194,913 A | * | 3/1993 | Myrick | G01N 21/65 250/458.1 |
| 5,953,169 A | * | 9/1999 | Tsai | G02B 26/008 359/889 |
| 6,509,567 B2 | * | 1/2003 | Boudet | G01M 3/002 250/343 |

FOREIGN PATENT DOCUMENTS

EP 0953838 A1 * 11/1999 ......... G01N 21/6452

* cited by examiner

*Primary Examiner* — Mark R Gaworecki
(74) *Attorney, Agent, or Firm* — Matthew J Patterson

(57) ABSTRACT

Apparatus and methods for performing optical analyses in a harsh environment are disclosed. Some of the systems and methods of the present disclosure include fluorescence, absorption, and reflectance detection using a drum spectrometer. Other systems and methods of the present disclosure include a measurement channel and a parallel reference channel concurrently filtering optical signals.

20 Claims, 13 Drawing Sheets

(51) Int. Cl.
  *G01N 33/28* (2006.01)
  *E21B 49/08* (2006.01)
  *E21B 49/10* (2006.01)
  *G01J 3/10* (2006.01)
  *G01J 3/14* (2006.01)
  *G01J 3/12* (2006.01)
  *G01N 21/17* (2006.01)
  *G01N 21/552* (2014.01)
  *G01N 21/43* (2006.01)
  *G01J 3/02* (2006.01)

(52) U.S. Cl.
  CPC . *G01J 3/10* (2013.01); *G01J 3/12* (2013.01); *G01J 3/14* (2013.01); *G01N 21/645* (2013.01); *G01N 33/2823* (2013.01); *G01J 3/0218* (2013.01); *G01J 2003/1213* (2013.01); *G01N 21/43* (2013.01); *G01N 21/552* (2013.01); *G01N 2021/1734* (2013.01); *G01N 2021/6471* (2013.01)

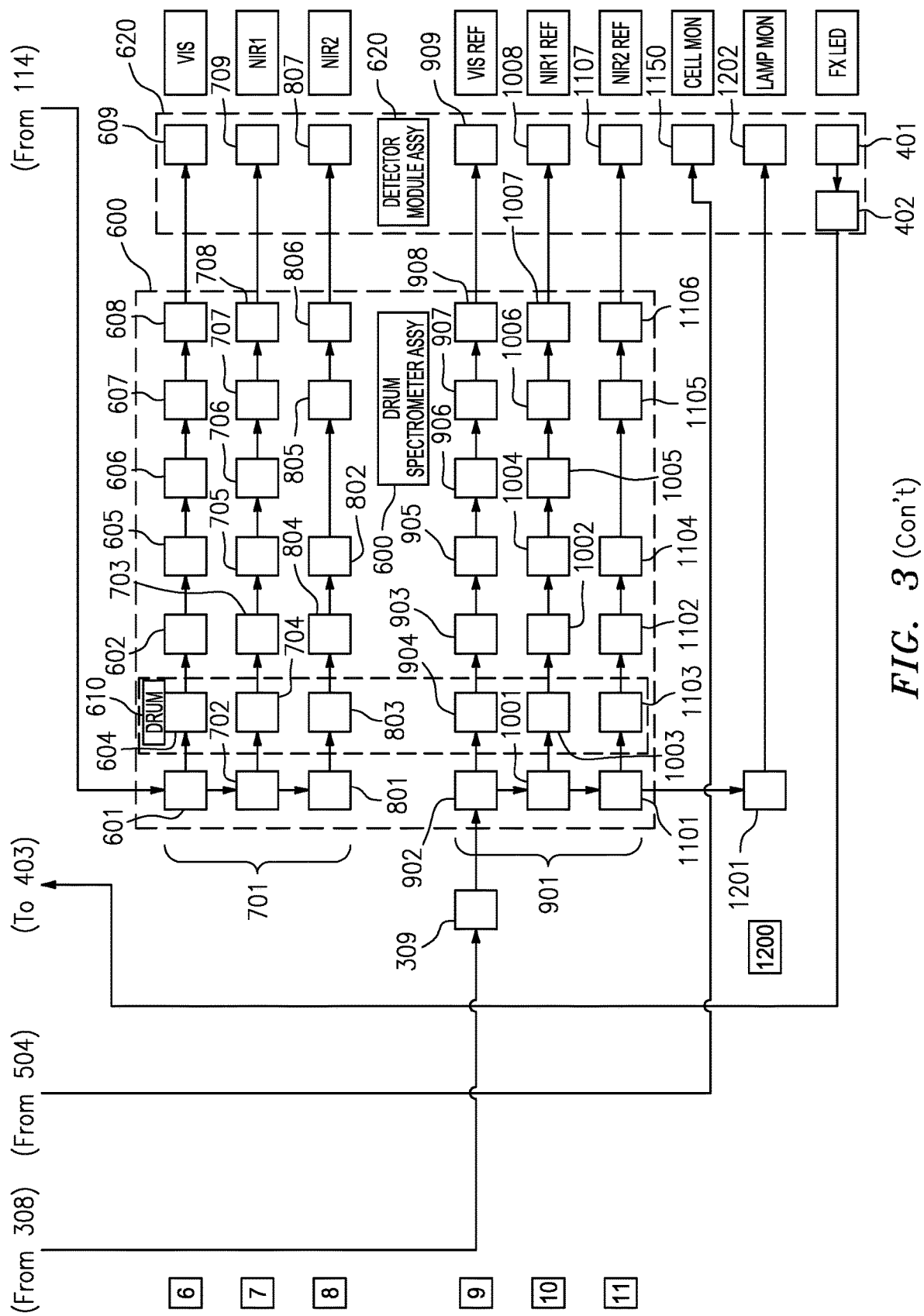
FIG. 3 (Con't)

OPTICAL FLUID ANALYZER

CROSS-REFERENCE TO RELATED APPLICATIONS

This application claims the benefit of U.S. Provisional Patent Application Ser. No. 62/463,357 filed 24 Feb. 2017. The disclosure of the application above is incorporated herein by reference in its entirety.

BACKGROUND OF THE INVENTION

Field of the Invention

Embodiments of the present disclosure generally relate to tools and techniques for performing analyses and characterization of substances within harsh environments. More particularly, the present disclosure relates to tools for performing in-situ analyses and characterization of substances utilizing optically based modules.

Description of the Related Art

Optical analyzers are used to characterize substances in many areas of art. The typical optical analyzer can comprise a spectrometer and is suitable for use in a controlled environment, such as a laboratory. There are a myriad of applications for optical analyzers for use in a harsh environment such as the nuclear and chemical processing, and oil and gas industries. Such harsh environments may have high temperatures and pressures and may also include caustic, volatile, or other materials that are harmful to electronics.

In the oil and gas industry, as an example of a harsh environment, wireline formation testing tools are well known in the prior art in providing permeability, mobility, sampling, and other information that can be inferenced therefrom about the reservoir. It is known that companies involved in the production of hydrocarbons strive to produce as much of the reserves within any given formation as possible. At the beginning of the life cycle of a well, wireline formation testers are used to determine many factors that predict how the well will perform. Later in the life cycle of a well, the production rate will taper off for many known and unknown reasons such as water break through, decreased porosity, mobility, and permeability among others.

Wireline formation testers of the prior art have included various testing modules to provide physical fluid property measurements, in-situ, for fluids in the borehole and the reservoir. These prior art methods have included resistivity measurements, pressure-volume measurements, nuclear magnetic resonance, and optical based sensors, among others. Early on, optical based sensors were primarily used to provide quantitative information about the oil-water fraction in wells drilled with water based mud and to distinguish between drilling mud and production fluid in wells drilled with oil-based muds. These measurements were done to determine when the flow line in a testing tool was sufficiently clear of invading fluids to obtain a sample representative of the reservoir. Other early optics-based measurements of the prior art include a bubble point detector and was also aimed at controlling the quality for sampling.

Downhole fluorescence sensors are also known in the prior art which typically comprise a narrow (or single) band source and multiple detectors usually in the visible light range. Some production fluids do fluoresce in the presence of such light and in some instances, such fluorescence sensor can distinguish oil-based drilling mud from naturally occurring production fluids. Other uses of fluorescence sensors include bubble point detection and phase detection.

Prior art optical analyzers included spectrometers to measure the absorption and/or the reflection of broadband light. Refraction spectrometers direct light through a window and onto the fluid within a flow line at a known angle of incidence. The refraction spectrometers typically use detectors to measure the intensity of the reflected light at different angles of incidence to determine the phase of the fluid flowing in the flow line. Such refraction spectrometers are sometimes referred to as "gas flags" because they are primarily used to determine the presence of gas bubbles in the flow line. An example of a refraction-type spectrometer is disclosed in U.S. Pat. No. 5,201,220 to Mullins, the disclosure of which is included herein in its entirety.

Absorption spectrometers of the prior art use detectors, or detector and filter pairs, which are selected based on a particular wavelength of interest and they measure the amount of light that the fluid within the flow line absorbs at the preselected wavelengths. The broadband light source can include wavelengths from the ultraviolet range (100-400 nm), the visible light range (400 nm to 800 nm) and the near infrared range (up to 2200 nm). Each such detector or filter and detector pair is commonly referred to as a channel. Fluids within the flow absorb light based on two phenomena: electronic absorption at shorter wavelengths and molecular absorption at longer wavelengths. At the shorter wavelengths, the fluids may absorb the light based primarily on color and convert the absorbed light to emitted light and heat. At longer wavelengths (lower frequencies), the light causes vibrations at the molecular bond level and local peaks of absorption occur at certain natural frequencies of these bonds. Absorption spectrometers of the prior art are useful in distinguishing between, and sometimes quantifying, water, oil, and drilling mud in a mixture of fluids. As discussed above, the channels are selected to provide information on the fluids that are predicted to be encountered. For instance, it is known that oil generally has a strong peak at about 1725 nm and water generally has two peaks, one at about 1445 nm and one at 1930 nm. The greater the number of channels that a spectrometer has the more complete a spectrum of the fluid mixture it can provide. Because of the size and availability of filters and the space limitations of downhole tools, prior art spectrometers typically have between eight and 20 channels. The limited number of channels may allow a spectrometer to distinguish between fluid types in the flow line but they do not have the spectral resolution to distinguish between different fluids of the same type. For instance, two production fluids coming from different reservoirs will have slightly different spectra. Typically, and as discussed above, samples of production fluids are taken from different locations within a borehole using wireline formation tools and the samples are analyzed using laboratory spectrometers to provide a continuous spectrum of the fluid thereby producing a fingerprint of the production fluid. Fingerprinting of the production samples allows users to determine whether there is more than one reserve along the borehole and whether there is connectivity between the reserves.

Therefore, there exists a need for providing in-situ, real time information related to fluid characterization in a harsh environment in the form of a comprehensive optical-based fluid analyzer.

SUMMARY OF THE INVENTION

In accordance with some aspects of the present disclosure, methods and systems related to an optical analyzer are presented.

It is an aspect of the present disclosure to provide an apparatus deployable in a harsh environment for fluid analysis having an electromagnetic source generating an optical signal across a spectrum of wavelengths, a source splitter optically coupled to the source and splitting the optical signal into a parallel reference channel and a measurement channel, where the measurement channel includes a test cell and wherein the optical signal of the measurement channel interacts with a fluid sample in the test cell, and at least one adjustable filter assembly having a plurality of filters mounted thereon, the plurality of filters including a parallel reference set of filters and a measurement set of filters, filtering the parallel reference channel with the parallel reference set of filters and filtering the measurement channel with the measurement set of filters and the at least one adjustable assembly adjustable to change which of the parallel reference set of filters filter the parallel reference channel and which of the measurement set of filters filter the measurement channels. The apparatus further includes at least one drive operable to move the at least one adjustable assembly, a control device electrically coupled to the at least one drive, the control device controlling movement of the at least one adjustable assembly; and a detection unit comprising a parallel reference set of detectors and a measurement set of detectors, the parallel reference detectors detecting the parallel reference channel after filtering with the parallel reference set of filters, and the measurement set of detectors detecting the measurement channel filtering with the measurement set of filters.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

The present disclosure is an optical fluid analyzer (OFA), and, when combined with equipment in a harsh environment, it can be utilized to analyze and characterize substances in the harsh environment.

For example, and without limiting the scope of the present disclosure to any area of art, when an OFA of the present disclosure is combined into a formation dynamic testing (FDT) tool, it can be utilized for analyzing and characterizing formation fluids in a downhole environment. Various embodiments of an OFA in accordance with the present disclosure include at least one optical sensor assembly for determining at least one property of a fluid from a hydrocarbon-producing well. As will be described more fully herein after, the OFA of the present disclosure may include a plurality of test cells including an absorption cell assembly, a fluorescence cell assembly, a fluid reflectance assembly, and may further include a spectrometer assembly, as well as various references and monitoring assemblies. The absorption cell may advantageously provide a spectrum of absorption levels versus intensity of light absorbed by the fluid and provide information allowing the identification of various constituents in a mixture of fluids that comprise the formation fluid. The fluorescence cell may, in addition to providing for identifying the bubble point of the formation fluid, sometimes provide information allowing for the identification between drilling mud (filtrate) and formation production fluid. The reflectance cell provides information important to the presence of gas within the formation fluid as well as identifying the presence of condensate, determining between rich gas and lean gas. In some embodiments of the present disclosure, multiple optical sensor assemblies may advantageously be combined together. The present disclosure may also include a cooling system capable of providing cooling to the OFA module 32 after a predetermined temperature is reached to maintain portions of the analyzer within a predetermined operating range to ensure adequate signal-to-noise ratio, accuracy, and reliability of the various components.

Figure 1:
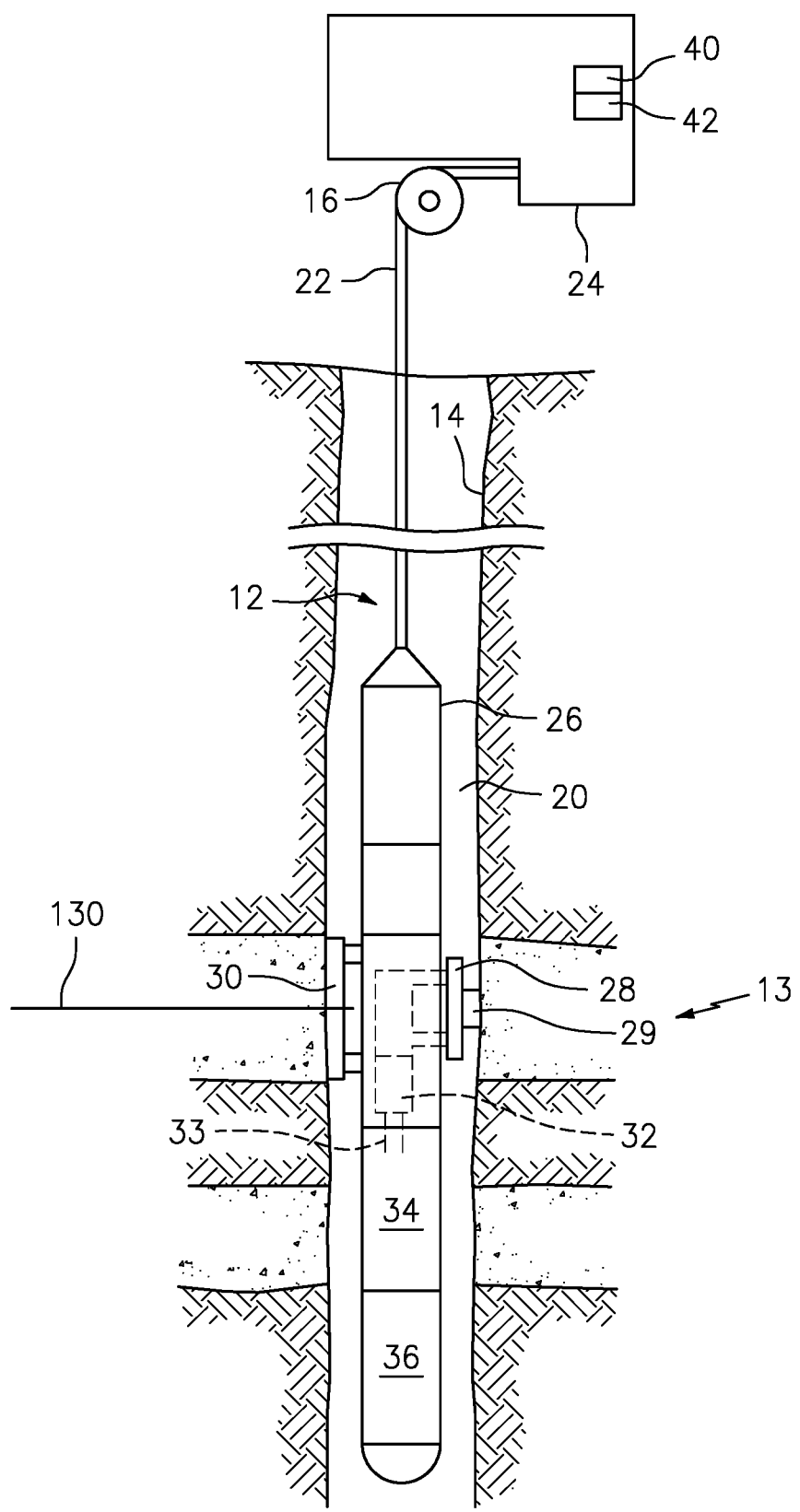
FIG. 1 is a schematic representation of an exemplary formation tester for analyzing downhole formation fluids in accordance with certain aspects of the present disclosure.

Examples of Tools for Monitoring, Analyzing and Characterizing Downhole Fluids With reference to FIG. 1, there is shown an embodiment of a wireline formation tester 20 deployed within a well 12 drilled into formation 13. In operation, wireline formation tester 20 is deployed into well 12 via wireline cable 22 over pulley 16. As is well known in the art, wireline cable 22 includes electrical conductors for powering the tool, data communication conductors, as well as tensile members for supporting the weight of the testing tool. The borehole typically contains various mixtures of fluids and gases wherein the mixture varies by depth, age of the well, and various other factors. The well is shown as an open hole, however, the present disclosure is not limited to open hole wells and could, for instance, be used within a cased hole well.

Still referring to FIG. 1, an embodiment of a formation tester 20 of the present disclosure is shown wherein the tool is deployed in a well 12 and includes various modules as will be described in more detail herein below. The wireline cable 22 can be a multi-conductor that carries electrical power and data to and from power and processing unit 24 located at the surface. The power and processing unit includes the capability to control the various modules included in the formation tester 20. In addition, power and processing unit 24 includes a processor 40, in the form of a computer and the like, for processing the electrical signals from the tool into information concerning the analysis and characterization of the downhole fluids as well storage medium 42. In this particular embodiment, the formation tester 20 includes a clamping mechanism 30 that is urged against the borehole wall 14 by pistons to stabilize the formation tester against the borehole wall 14. The formation tester includes a probe assembly 28 having a mechanism to urge the probe pad against borehole wall 14 with sufficient force to releasably fix the formation tester in place at preselected test position 130. The probe assembly 28 and the clamping mechanism 30 are configured so that the formation tool does not rotate or wobble in the preselected downhole position. The probe pad further seals the formation 13 from the wellbore 12 in the area of contact with borehole wall 14. The snorkel 29 of probe assembly 28 seals against, and can penetrate, the borehole wall 14 and any mudcake that may exist adjacent thereto and enters the formation 13. The snorkel 29 is in hydraulic communication with pump out module 36 wherein the pump is mounted (not shown) within the formation tester housing 26 wherein a flowline presents reservoir fluid to OFA module 32 for monitoring and analysis as will be more fully described herein below. Although the order of OFA module 32 and modules 34 and 36 are as shown, it is within the scope of the present disclosure that OFA module 32 may be mounted within other modules and in other configurations, such as above the probe assembly 28, without departing from the scope of the present disclosure. The probe assembly 28 may also include a guard ring (not shown), which may comprise a loop that encircles the ring, and is hydraulically coupled to a pump. An exemplary embodiment of a focused guard probe is disclosed in U.S. Pat. No. 6,301,959 ('959) to Hrametz. The pump out module 36 moves fluids from formation 13 through OFA module 32 for analysis as will be more fully explained herein below.

Figure 2:
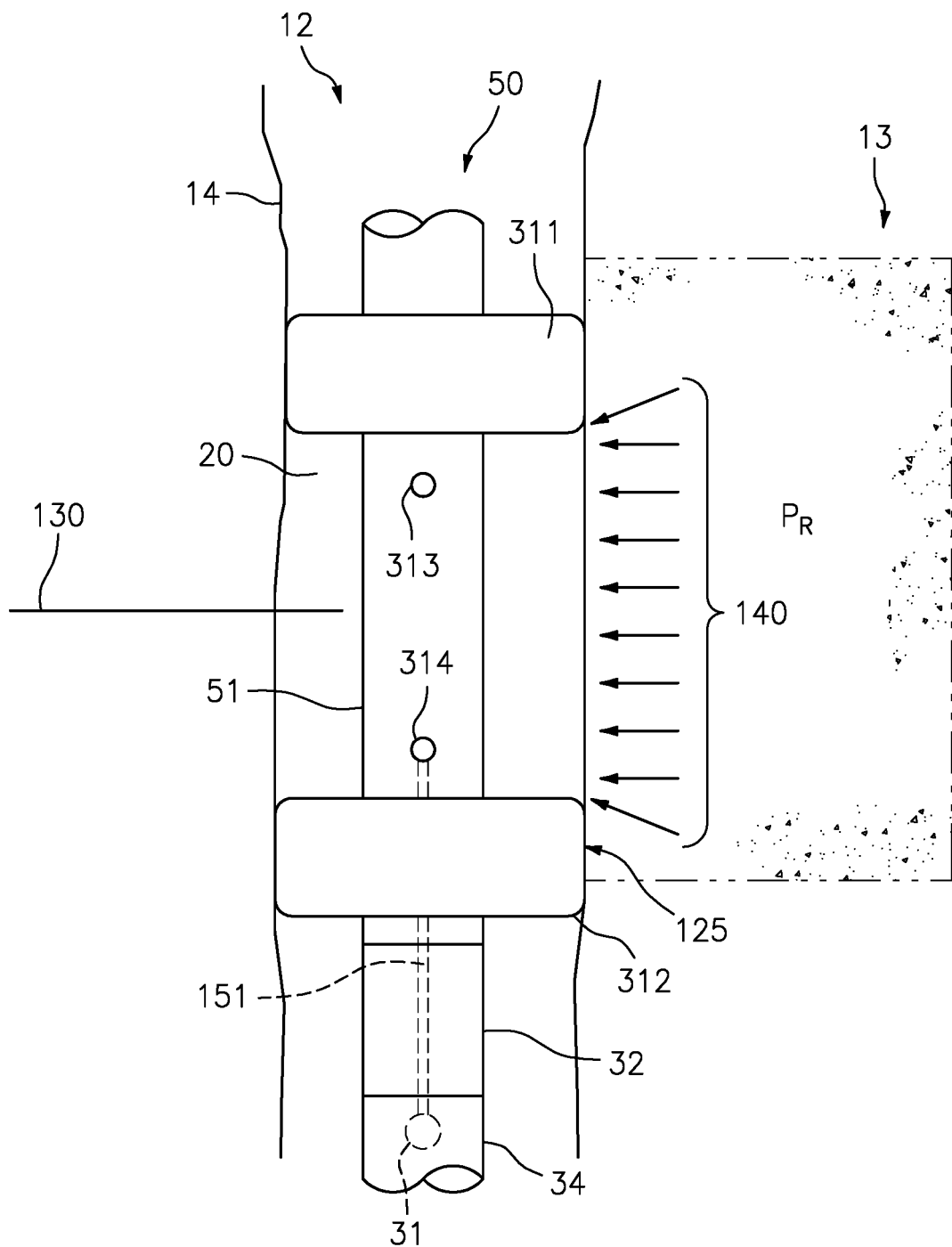
FIG. 2 is a schematic representation of an exemplary formation tester for analyzing downhole formation fluids in accordance with certain aspects of the present disclosure.

Another embodiment of the present disclosure further includes formation testing tool 50 shown in FIG. 2 wherein the tool is deployed in well 12 and includes a pair of spaced apart straddle packers 311, 312. In this particular embodiment, the straddle packer pair 311, 312 are positioned about one meter apart and seal against tool housing 51 and are inflated to seal against borehole wall 14 as is known in the industry to stabilize the formation tester within the wellbore 12. The pump 31, shown within module 34 pumps fluid from formation 13 into one or both of inlet 314 and inlet 313 and through OFA module 32 and through flow line 151. As discussed herein with respect to FIG. 1, the specific order and the orientation of OFA module 32 and other modules does not depart from the present disclosure. Reservoir fluids are analyzed as pump 31 moves fluids from formation 13 through OFA module 32 as will be more fully explained herein below. OFA module 32 will be discussed generally herein below and with reference to the embodiment shown in FIG. 1 but such description applies to the embodiment of OFA module 32 shown in FIG. 2.

Example Light Paths for an Optical Fluid Analyzer

Figure 3:
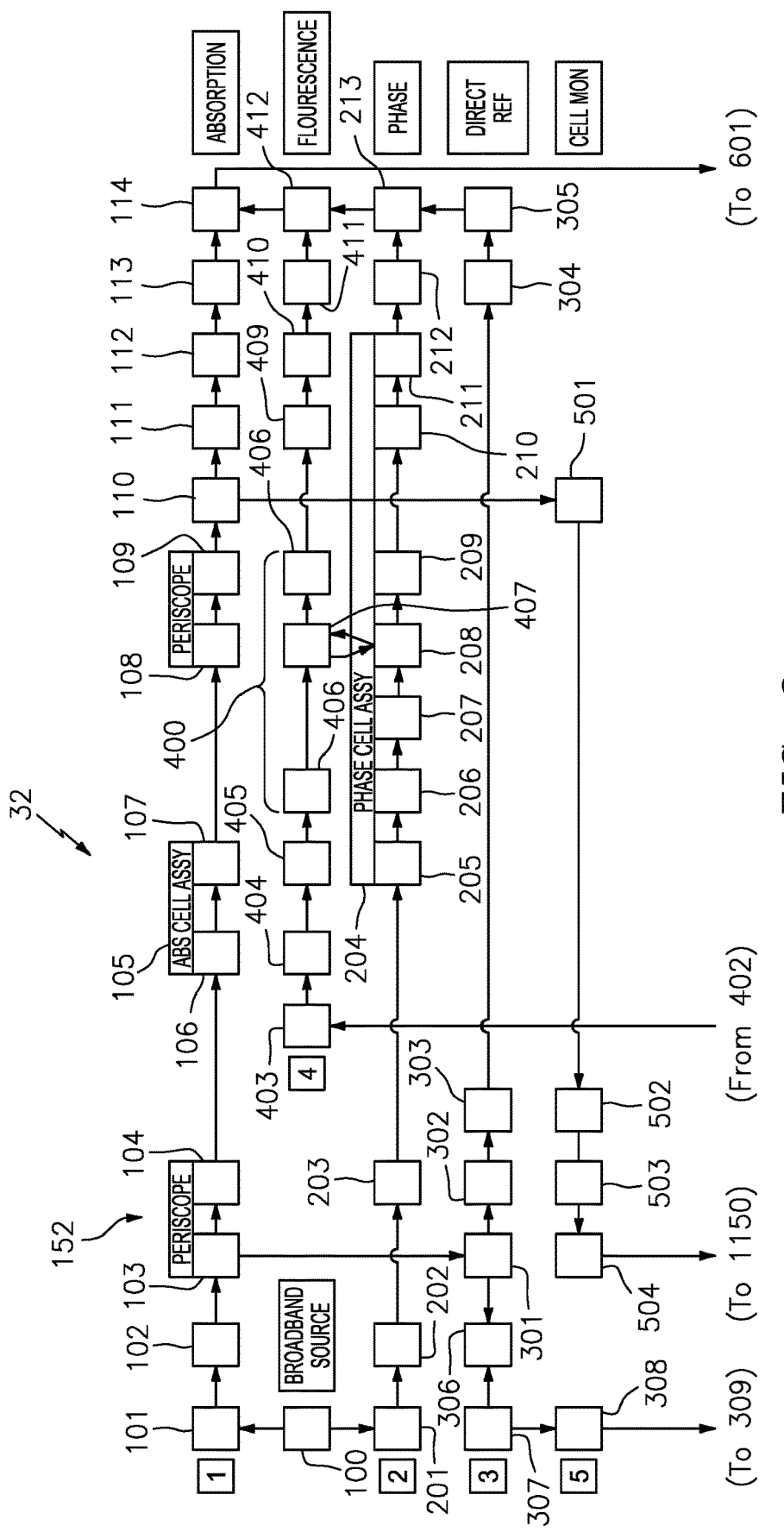
FIG. 3 is a schematic representation of the light paths for various optical components of an optical fluid analyzer in accordance with certain aspects of the present disclosure.

With reference to FIG. 3, the logical flow of light paths for various optical assemblies of an OFA module 32 in accordance with an embodiment of the present disclosure will be described. In the embodiment shown, OFA module 32 functionally includes absorption spectroscopy, fluid reflectance spectroscopy, and fluorescence spectroscopy. The various mirrors, splitters, and other elements known in the art described herein are needed to route the light through the embodiments described, wherein different types and arrangements of optical elements may be used in other embodiments without departing from the scope of the present disclosure. OFA module 32 includes a broadband light source 100 for the spectrometer, as will be described more fully herein below. Light source 100 may advantageously comprise a halogen light bulb with a black body temperature of about 2900 K and in certain embodiments of the present disclosure the light source remains energized during the entire measurement sequence at the preselected depth of test position 130 (FIG. 1). Following light path 1 in FIG. 3, directed at absorption spectroscopy, light from source 100 is directed by mirror 101 to a relay lens 102 and in this particular embodiment, into a beam splitter 103. It should be appreciated by those skilled in the art that the beam splitter, as well as other components described herein, should comprise broadband, low loss or lossless qualities to preserve the intensity and spectrum of the light emitted by source 100. A portion of the light is directed into a beam splitter 301, which further divides the light between the parallel reference filter assembly 901, a portion of which goes to the lamp monitor detector 1202, and toward the direct reference/measurement filter assembly channel set 701 as will be described herein after. The remainder of the light from source 100 is directed by mirror 104 to absorption cell 105 having windows 106 and 107 defining a gap between them accommodating a flow stream. The operation and arrangement of physical components of the absorption cell will be described in more detail herein after. Some of the light may be absorbed in the cell and the remainder is directed to mirrors 108 and 109 and onto beam splitter 110 wherein a portion is directed to cell monitoring light path 5, which will be described in more depth herein after. The remainder of the light is directed to relay lens 111 and directed on shutter 112. Shutter 112 may comprise a solenoid bi-stable shutter, suitable for operation at elevated temperature. Shutter 112 is actuated (opened) every time an absorption measurement is required. The shutter is closed every time a dark measurement, a fluid reflectance, or a direct reference measurement is performed. In an embodiment of the present disclosure, the actuation duration is about 30 ms.

Light emitted from shutter 112 is relayed by lens 113, directed to beam splitter 114, and directed, along with light from other assemblies, to the measurement set of channels 701 of the drum spectrometer assembly 600.

Still referring to FIG. 3 and following light path 2, directed at fluid reflectance detection, light from broadband source 100 is directed to mirror 201 and onto relay lens 202 wherein it is directed onto shutter 203. Shutter 203 is actuated (opened) every time a fluid reflectance measurement is required. It is closed every time a dark measurement, an absorption measurement, or a direct reference measurement is performed. The actuation duration is about 30 milliseconds. Light from shutter 203 is directed to reflectance cell 204 wherein the reflectance cell comprises mirror 205, polarizer 206, cylindrical lens 207, prism 208, a second cylindrical lens 209, a linear variable filter 210 and mirror 211. The operation and arrangement of physical components of the reflectance cell will be described in more detail herein after. The polarizer 206 may comprise a p-polarizer or an s-polarizer. In this particular embodiment, an s-polarizer is shown. The broadband light is focused into a line by cylindrical lens 207 and directed onto an angled surface of prism 208 and becomes incident at the interface between the sapphire window (similar to that described herein above with reference to absorption cell 105) and the fluid. The converging beam of light covers a range of angles of incidence. Depending on the refractive index of the material in the flow stream (liquid, gas, or mixture), only the rays which have an angle of incidence greater than the critical angle will be reflected. In the embodiment shown in FIG. 3, the reflected portion of the light exits a second angled surface of the prism 208, is directed through a second cylindrical lens 209 and onto linear variable filter 210. As the source is broadband, a linear variable filter 210 (LVF) is used to spectrally encode the reflected angles of the light. The angle of the reflected light is therefore easily determined based on its unique spectral encoding. It should be appreciated by those skilled in the art that the LVF 210 could be placed before the window 106 to encode the angles of incidence with wavelength. Lens 212 directs the encoded light to beam splitter 213 where it is further directed to a spectrometer. Decoding is performed by the spectrometer wherein discrete filters are arranged therein having wavelengths that are able to detect the encoded wavelengths and determine the angle of incidence thereby as will be more fully described herein after.

This particular embodiment of the present disclosure further includes fluorescence spectroscopy including a fluorescence measurement cell 400 (FMC) depicted schematically in light path 4 of FIG. 3. Light from LED 401 can produce a fluorescence excitation, and in this particular embodiment the LED comprises a blue LED 401 having a wavelength between 457 nm and 463 nm, is injected into a doped 600 μm optical fiber 402 having a numerical aperture of 0.22 and directed to collimating lens 403 and discrete filter 404. Discrete filter 404 separates the excitation spectrum of the LED from the expected fluorescence spectrum, so that excitation is not mixed with fluorescence light emitted from the flow stream. Mirror 405 directs the light into FMC 400 and, in transmission, dichroic beam splitter 406 directs blue light, the fluorescence excitation, through focusing lens 407. The embodiment of FMC 400 shown is commonly referred to as epifluorescence and the dichroic beam splitter 406 transmits the excitation light to the sample and simultaneously reflects only the emitted light (reflected fluorescence signal) from the fluid stream back to light path 4. The fluorescence excitation light is projected through a flat portion of prism 208 and becomes incident at the interface between the sapphire window and the fluid in the flow stream. An emitted fluorescence signal may be emitted back to focusing lens 407 depending on the type of material in the flow stream. The emitted fluorescence signal directed back through focusing lens 407 is passed to dichroic beam splitter 406 where mirror 409 directs the light to discrete filter 410 wherein the filter only allows the emitted fluorescence signal to pass onto beam splitter 412. The emitted fluorescence signal is further directed to a spectrometer and onto a detector.

Referring now to light path 3 of FIG. 3, there is shown a portion of the light path for a direct and a parallel reference. The reference paths measure the spectrum of the light source 100 (light bulb) that may affect measurement quality as will be explained in more detail herein below. Among other things, the reference signals are used to normalize the differences between detectors and absorption signals in accordance with an embodiment of the present disclosure. Broadband light from light source 100 is directed from beam splitter 103 and is further directed to beam splitter 301. A portion of the light, comprising the direct reference, is directed to shutter 302 which is actuated every time a direct reference measurement is required, wherein the direct reference light signal is relayed by lens 303 and directed by mirror 304 to focusing lens 305, where it is further directed to measurement set of channels 701 of drum spectrometer 600. Shutter 302 is closed every time a dark measurement, an absorption measurement, or a fluid reflectance measurement is performed. The remainder of the light from beam splitter 301 comprises the parallel reference light and is directed by mirror 306 to a relay lens 307 into a 400 μm optical fiber 308 having a numerical aperture of 0.22 and passes through lens 309, where it is further directed to parallel reference channels 901 of drum spectrometer 600.

A cell monitor of the present disclosure is described with reference to light path 5 in FIG. 3, wherein a portion of the light that is transmitted through absorption cell 105 is directed by beam splitter 110 to mirror 501, that in turn directs the light to discrete filter 502 and onto lens 503 to direct the light into optical fiber 504. The cell monitor of light path 5 continuously monitors the overall absorption of light by the fluid in the absorption cell 105 and gives a continuous signal indicative of the gross intensity of light transmitted through the absorption cell. The light transmitted on light path 5 is directed to detector 1150. Signals sent to the processing unit from detector 1150 are integrated over a given spectral range, determined by the source emission spectrum and filters used. Fast fluctuations of the intensity of the cell monitor signal may indicate the presence of gas bubbles, slugs, contaminants, or a multiphase flow flowing in the flow line. Optical fiber 504 comprises a 600 μm fiber having a numerical aperture of 0.22 which is used to direct the unabsorbed light from absorption cell 105 to detector 1150 of detector module 620. The detector module 620 will be described in greater detail herein after.

Still referring to FIG. 3, the OFA module 32 of the present disclosure includes a drum spectrometer assembly 600 to measure the intensity of light at specific wavelengths from the various light paths described herein above. Spectrometer assembly 600 comprises a drum 610 that is rotated during operation, wherein the drum includes discrete optical filter assemblies 604, 704, 904, and 1003 as well as angle tuned filter assemblies 803 and 1103. As will be described in more detail herein after, the spectrometer 600 comprises two sets of three channels represented schematically in the first measurement set of channels 701 as light paths (channels) 6, 7 and 8 and the second, parallel reference, set of channels 901 as light paths, or channels, 9, 10, and 11, respectively. In certain embodiments, channel set 701 is spectrally identical to channel set 901, with the only physical difference in the mirror 801 in channel set 701, and a beam splitter 1101 in channel set 901, in which the beam splitter directs a portion of the light to lamp monitor detector 1202 of detector module 620. The remaining portion of light from beam splitter 1101 follows a path 11 which is identical to light path 8 of channel set 701. The six light paths are fixed. As the drum rotates, the light paths are presented to a different discrete filter, each at different wavelengths, and the angle of incidence is swept on the angle tuned filters, in essence, sweeping the transmitted wavelength.

With reference to drum spectrometer assembly 600, light from the absorption cell 105, the fluorescence measurement cell 400, the reflectance cell 204, and the direct reference signal (of light path 3) are directed to first set of measurement channels 701 of the drum spectrometer assembly wherein the light is filtered into various spectral ranges and its intensity is measured. The light is first received by dichroic beam splitter 601 and is directed to filter 602 allowing light in the visible and near infrared range, from approximately 380 nm to approximately 875 nm, there through (the remainder of the light is directed toward dichroic beam splitter 702). The light enters discrete optical filter assembly 604, which includes six fixed filters at different wavelengths of interest (434 nm, 500 nm, 600 nm, 700 nm, 780 nm and 850 nm) and directs the filtered light by wavelength through mirror pair 605 and 606 to lens 607 which couples the light into optical fiber 608. The six filters that comprise optical filter assembly 604 are mounted to within drum assembly 600 (FIG. 10) wherein the light is presented to the different filters as they rotate past the incident light as will be more fully described herein below.

The direct reference signal of light path 3 is used in conjunction with light path 1 to determine the amount of light that is absorbed within the fluid passing through the absorption cell 105. For example, if the direct reference signal has a value of 250, as determined by detector module 620, and the absorption signal from light path 1 has a value of 125, as determined by detector module 620, then the fluid has absorbed 50% of the light, at the considered wavelength. It should be appreciated by those skilled in the art that the amount of absorption at a given wavelength yields information that may aid in the identification of the fluid. An optical fiber directs the light spectra to the detector assembly as will be described more fully herein below.

The light directed from dichroic beam splitter 601 to dichroic beam splitter 702 is directed to filter 703, allowing light in the infrared and near infrared range, from approximately 910 nm to approximately 1530 nm, and above 1860 nm, there through (the remainder of the light is directed toward mirror 801). The light enters discrete optical filter assembly 704, which is similar to discrete optical filter assembly 604 described herein above, which includes six fixed filters at different wavelengths of interest (935 nm, 1080 nm, 1290 nm, (1450 nm or 1930 nm for water ($H_2O$) measurement), 2013 nm (for carbon dioxide ($CO_2$) measurement), and 2045 nm (for $CO_2$ baseline measurement) and directs the filtered light by wavelength through mirror pair 705 and 706 to lens 707, which couples the light into optical fiber 708. The optical fiber directs the near infrared light spectra to the detector assembly as will be described more fully herein below.

The light that passes from dichroic beam splitter 702 mainly comprises light having many wavelengths in the near infrared range, from approximately 1530 nm to approximately 1860 nm, and it is directed down light path 8 to mirror 801 and onto filter 802, wherein light in the wavelength range of about 1530 nm to approximately 1860 nm is allowed to pass there through. The light enters angled tuned filter assembly 803, which includes two angled tuned filters targeted for capturing hydrocarbon composition measurements between 1550 nm and 1830 nm, the "oil window".

The angle tuned filter assembly 803 is mounted within drum spectrometer 600 (FIG. 10) which sweeps the angle of incidence on the angled filters. In an embodiment of the present disclosure, the angle tuned filters of angle tuned filter assembly 803 comprise a pair of angled tuned filters whose output is measured at 4 nm increments between each measurement. It should be appreciated by those skilled in the art that this particular embodiment of the present disclosure provides for 70 increments between 1550 nm and 1830 nm, with a 10-15 nm resolution, and that such a fine sampling interval yields a highly refined spectral sample in the area of interest. The filtered light is directed through mirror 804 to lens 805 which couples the light into optical fiber 806. The optical fiber 806 directs the near infrared light spectra to detector 807 of detector assembly 620 as will be described more fully herein below.

With reference to the second set of channels, the parallel reference set 901 of drum spectrometer assembly 600, broadband light from optical fiber 308 is directed through lens 309 and passed through dichroic beam splitter 902 to filter 903 wherein light having wavelengths in the visible range, from approximately 380 nm to approximately 875 nm, is directed down light path 9 (the remainder of light is directed toward dichroic beam splitter 1001). The light enters discrete optical filter 904 (identical to 604), which includes six fixed filters at different wavelengths (434 nm, 500 nm, 600 nm, 700 nm, 780 nm, and 850 nm) used to make color correction normalization and directs the filtered light by wavelength through mirror pair 905 and 906 to lens 907 which couples the light into optical fiber 908. The optical fiber directs the visible light spectra to the detector assembly 620 as will be described more fully herein below.

The light from dichroic beam splitter 902 is directed to dichroic beam splitter 1001 and to filter 1002 wherein light having wavelengths in the near infrared range, from approximately 910 nm to approximately 1530 nm and beyond 1860 nm, is directed down light path 10 (the remainder of light is directed toward beam splitter 1101). The light enters discrete optical filter 1003 (identical to 704), which includes six fixed filters at different wavelengths of interest (935 nm, 1080 nm, 1290 nm, 1450 nm (or 1930 nm), 2013 nm, and 2045 nm) and directs the filtered light by wavelength through mirror pair 1004 and 1005 to filter 1006, which couples the light into optical fiber 1007. The optical fiber directs the near infrared light spectra to the detector assembly as will be described more fully herein below.

The light that passes from dichroic beam splitter 1001 is comprised of light having many wavelengths and is directed to filter 1102, allowing light in the infrared range, from approximately 1530 nm to approximately 1860 nm, to pass there through. The remainder of the light is directed toward lens 1201 and light path 1200. The light from filter 1102 enters the angled tuned filter assembly 1103 (optically identical to 803), which includes two angled tuned filters between 1550 nm and 1830 nm, that sweep the angle of incidence to provide hydrocarbon composition measurement normalization. The filtered light is then directed by mirror 1104 to lens 1105, which couples the light into optical fiber 1106. The optical fiber directs the near infrared light spectra to the detector assembly as will be described more fully herein below.

Still referring to FIG. 3, the OFA module 32 of the present disclosure includes a photo detector module assembly 620 to receive output from drum spectrometer 600. Detector module 620 comprises both silicon (Si) and indium gallium arsenide (InGaAs) photo detectors. Measurement set of detectors 609, 709, and 807 receive light that carries information about the fluid and reference set of detectors 909, 1008, and 1107 receive light that comprise the parallel reference signals. The light in the visible/near infrared (NIR) range from optical fiber 608 is shone onto detector 609. Detector 609 is a silicon-based detector that converts the light to an electrical signal. Similarly, light from optical fibers 708 and 806 are shone onto detectors 709 and 807, respectively. Detectors 709 and 807 are both InGaAs detectors that convert the light signals to electrical signals. The light in the visible/NIR range from optical fiber 908 is shone onto detector 909. Detector 909 is a silicon-based detector that converts the light to an electrical signal. Similarly, light from optical fibers 1007 and 1106 are shone onto detectors 1008 and 1107, respectively. Detectors 1008 and 1107 are both InGaAs detectors that convert the near infrared light signals to electrical signals. The converted signals are an analogue signal which is proportional to the intensity of the light that fall on them. The analogue signals are communicated to the processing unit in the OFA. It should be appreciated by those skilled in the art that the reference channel and the measurement channel are concurrently filtered through their respective plurality of filters.

A dark measurement is made when all light paths are blocked. It is an advantage of the present disclosure over the prior art in that light source 100 is on continuously and not switched off to make a dark measurement and switched back on again to make a fluid measurement. The switching on and off of a light source can bring stability errors and shorten the life of the source. This may occur in measurement channel set 701 by closing shutters 112, 203, and 302 and by further switching LED 401 into the off position. Dark measurements may also be made at points in the rotation of the drum 610 when light falls between filters as they rotate and is not transmitted out of the drum. The dark measurements measures the electrical noise of the detectors when they are not illuminated. The magnitude of the dark signal is subtracted from both the reference and the measurement signal, absorption signals for example, then the absorption signal is normalized (divided) by the reference signal as will be explained more fully herein below. Further signal processing may be applied (placing signals in wavelength bins) and then sent to the ground equipment 24 (FIG. 1) for display and/or further processing.

Example Monitoring and Measurement Cells of an Optical Fluid Analyzer

Figure 4:
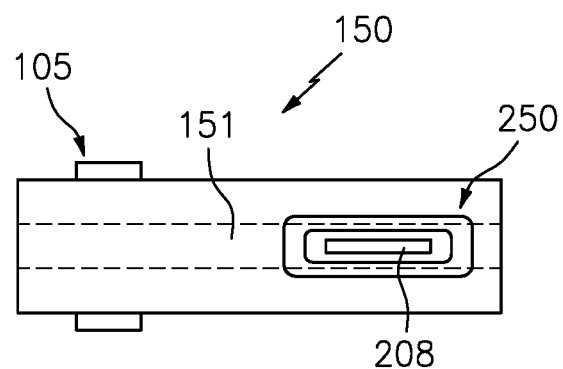
FIG. 4 is a top view of an optical chassis of an optical fluid analyzer in accordance with certain aspects of the present disclosure.
Figure 5:
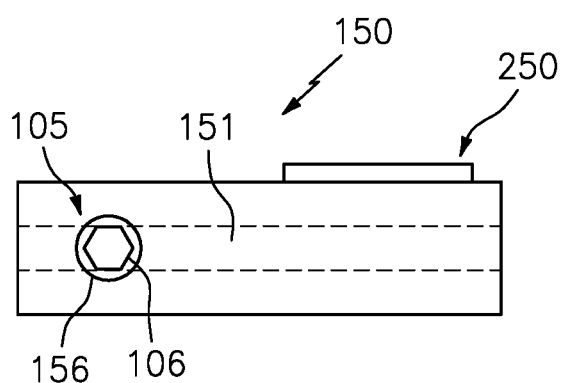
FIG. 5 is a side view of an optical chassis of an optical fluid analyzer in accordance with certain aspects of the present disclosure.
Figure 6:
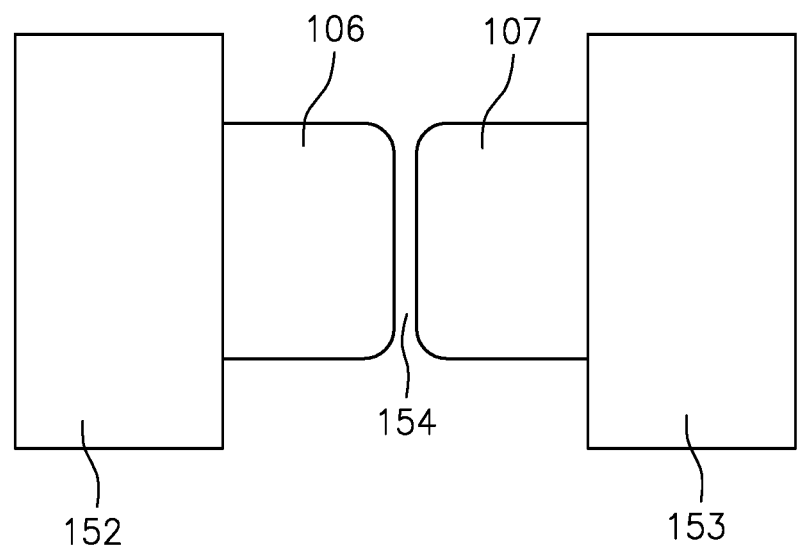
FIG. 6 is a view of a pair of windows of an absorption cell in accordance with certain aspects of the present disclosure.

The OFA module 32 shown in FIG. 1 includes various optical components that are optically coupled to an optical chassis 150 as is best shown with reference to FIGS. 4 and 5. Chassis 150 includes a flow line 151 that runs through the chassis and is hydraulically connected to snorkel 29 (FIG. 1), and is rigidly fixed within wireline formation tester 20 (FIG. 1), and carries formation fluid there through. Chassis 150 includes an absorption cell 105 and a prism assembly 250 which includes prism 208 (FIG. 3). With reference to the description directly herein above and FIG. 6, an example of the absorption cell 105 includes windows 106, which windows can be comprised of sapphire, and 107 mounted within carriers 152 and 153, respectively. FIGS. 4 and 5 depict flow line 151 shown in phantom within chassis 150. When windows 106 and 107 are mounted within absorption cell 105, a gap 154 of approximately 1-2 mm is formed there between. In the embodiment shown, the window carriers are secured within chassis 150 by hollow screws 156. It is an important aspect of the present disclosure that the formation fluids maintain their original pressure while the analyses are being performed. To that end, the cross-sectional area of flow line 151 inside of the absorption cell 105, taking into account the geometries of the chassis 150 and windows 106 and 107, is matched to that of the remainder of flow line 151 as depicted in FIGS. 4 and 5. Now referring also to FIG. 3, broadband light from source 100 is directed into window 106 via efficient angled mirror 108. There is an optical arrangement, in the form of a periscope solely as a means of directing light into and out of this particular embodiment, of mirror 109 connected to window 107 that receives the light that is transmitted through absorption cell assembly (that which is not absorbed by fluid in the flow line) and transmits that light to drum spectrometer 600.

Figure 7:
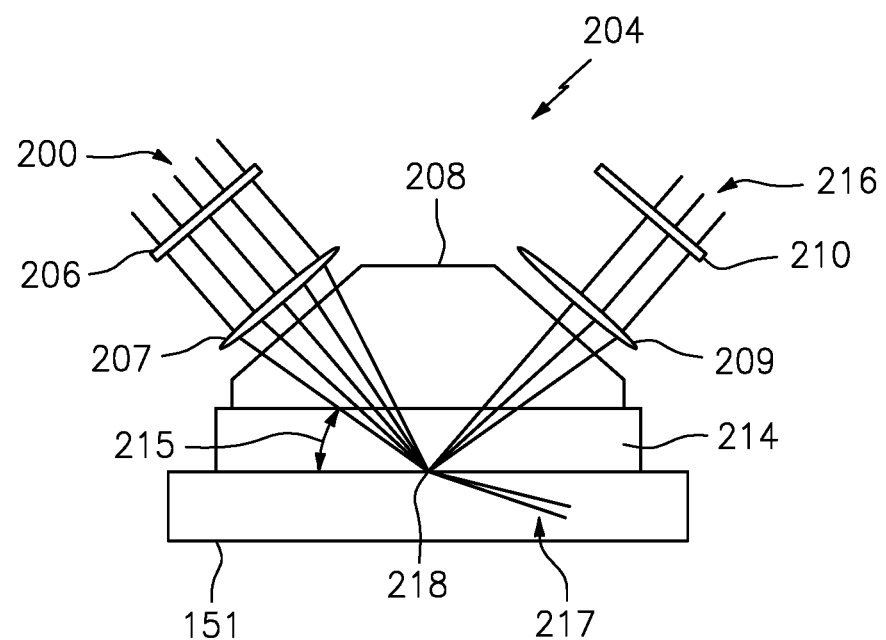
FIG. 7 is a schematic representation of a reflectance cell in accordance with certain aspects of the present disclosure.

The present disclosure also includes a reflectance cell 204 to help determine, for example, the presence of gas, and/or determining the gas-to-oil ratio, within a fluid in flow line 151. An example of a portion of the reflectance cell assembly, or refraction spectrometer, is shown in FIG. 7 wherein prism 208 is optically connected to sapphire window 214, which is in fluid contact with fluids in the flow line 151. Although depicted as separate components in the embodiment shown, prism 208 and sapphire window 214 may also comprise a monolithic structure.

Figure 8:
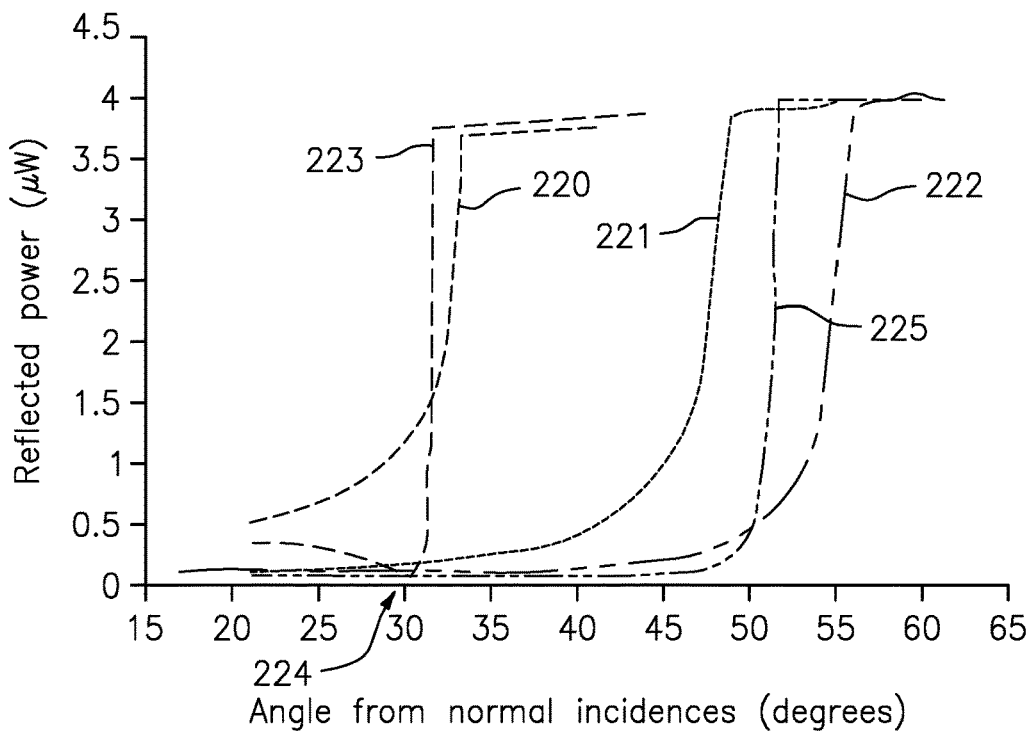
FIG. 8 is a graphical representation of the reflectance of various fluids in accordance with certain aspects of the present disclosure.

In reflectance cell 204, light 200 from source 100 (FIG. 3) is projected through cylindrical lens 207 and into prism 208. The light 200 passes through sapphire window 214, where it becomes incident on fluid within flow line 151. The light becomes incident with the fluid at a low angle of incidence 215 relative to the vertical axis in FIG. 7. In certain embodiments, the angle of incidence 215 will include a range of angles and may, for example, include angles of incidence 215 from 30 degrees to 50 degrees. Depending on the material in the flow line 151, some rays of the light 216 are reflected and some rays of the light are refracted 217. As discussed, reflectance cell 204 may detect the presence of gas within flow line 151, wherein gas has a refractive index close to 1.0 at the interface between the fluid and the sapphire window. All other liquids of interest will have a refractive index greater than 1. For example, water has a refractive index of approximately 1.3. This effect is best illustrated with reference to FIG. 8 and while still referring to FIG. 7, wherein the angle of incidence 215 influences the amount of light 217 refracted, and conversely the reflected light 216, for different fluids comprising gas 220, water 221, and oil 222, based on their respective different refractive indices for s-polarized light. Therefore, for small angles of incidence 215, more light will be absorbed/refracted 217 into the fluid as shown in FIG. 8. It is important to note that the curves shown in FIG. 8 are between about 20 degrees and about 60 degrees. When the power of the reflected light 216 approaches a maximum value, one can infer the presence of gas in flow line 151. The increasing presence of liquid, as opposed to gas, in flow line 151 is indicated as the power of the reflected light 216 drops in intensity with respect to respectively smaller angles of incidence 215.

Certain embodiments of the reflectance cell 204 of FIG. 7 the present disclosure implement an approach using the Fresnel reflection on the refractive index contrast and angle of incidence 215 to detect gas in flow line 151 using known methods such as those set forth in U.S. Pat. No. 5,167,149, the disclosure of which is incorporated by reference herein in its entirety. Certain embodiments of the present disclosure also utilize the basic properties of Fresnel reflection to discern information about a fluid in a borehole flow stream. However, the present disclosure includes advances over the prior art in that light 216 reflected from the sapphire-fluid interface 218 (FIG. 7) is further measured and analyzed, using the same detectors of drum spectrometer assembly 600 as is used in for other measurements, at a range of angles of incidence 215 as will be more fully described herein after. In addition, in the example shown, the polarizer 206 may advantageously comprise an s-polarizer wherein the light is polarized normal to the plane of incidence with the flow line 151 at point of interface 218. In FIG. 7, light 200 from broadband light source 100 is directed through s-polarizer 206, cylindrical lens 207 and prism 208, and the reflected light 216 is directed through a second cylindrical lens 209 and onto linear variable filter (LVF) 210. As one skilled in the art can appreciate, linear variable filter 210 is used to encode the reflected rays of light 216 with wavelength versus angular position data. The incident broadband light remains broadband after reflection, but only certain angles are reflected. Each reflected angle will reach the LVF at a different position whereupon only the corresponding specific wavelength of the filter is passed. Hence, each wavelength passed by the filter directly encodes an angle of incidence/reflection. The encoded light is directed to drum spectrometer 600 (FIG. 3) where the wavelength of the encoded light is detected and the angle can be readily determined. It will be appreciated by those skilled in the art that the approach of the present disclosure provides for greater measurement resolution over that used in the prior art.

As discussed above, and with reference to FIG. 7 and FIG. 8 the line indicating oil 222 shows the theoretical reflectivity at interface 218 between sapphire window 214 and oil, and the line indicating gas 220 shows the theoretical reflected power measurement (reflectivity) at interface 218 between the sapphire and material flowing in the flow line. The reflectivity depends on angle of incidence 215 and the polarization state (p or s) of the incident light. At angles of incidence greater than the critical angle, all light is reflected and none is transmitted into the flow line. At less than the critical angle, some light is transmitted and some light is reflected. An example of the present disclosure uses s-polarized light and an angular range of approximately 35° to 47° and FIG. 8 illustrates how this angular range facilitates differentiation between fluids comprising gas 220, water 221, and oil 222, based on their respective different refractive indices. In alternative embodiments of the present disclosure wherein the polarization state of the light is p-polarized, the differentiation between fluids may be more apparent. With p-polarized light, light is projected parallel to the plane of flow line 151 and there is a particular angle less than the critical angle, known as the Brewster angle and that allows nearly 100% transmission into the flow line. The values for Brewster and critical angles are significantly different between gas and oil and therefore measuring the relative intensity of the reflective power over a range of angles allows for the positive identification of gas. For instance, the reflectivity of gas 223 for p-polarized light passes through the Brewster angle 224 where the reflectivity is nearly zero (fully transmitted) and then makes an abrupt change in reflectivity near the critical angle when compared to the more gradual change of the s-polarized light indicating gas 220. Similarly, the reflectivity of p-polarized light for oil 225 is nearly all transmitted into the flow line 151 and the slope of the change in reflectivity is much steeper than the s-polarized reflectivity for oil 222. In other embodiments of the present disclosure, and as discussed herein above, s-polarized light may be used wherein the output may provide a smoother progressive curve allowing for better interpretation.

As discussed herein above with reference to light path 4 in FIG. 3, the present disclosure may advantageously include fluorescence measurement cell 400 to assist in analyzing and characterizing downhole fluids. With reference to both light path 4 in FIG. 3 and FIG. 9, the example shown utilizes an epifluorescence approach, a well-known technique where excitation of the fluorophore in a fluid (if present) and detection of the fluorescence are done through the same light path. In the present disclosure, the fluorescence excitation from LED 401, shown as injected excitation light 414, is directed through focusing lens 407 and injected into the flat, top, portion 413 of prism 208, through sapphire window 214 and becomes incident normal (perpendicular) to the fluids in flow line 151 at the point of interface 218. If the fluid flowing in flow line 151 contains a fluorophore, i.e. is of the type that is able to fluoresce, given the excitation light 414, the fluorescence signal 415 is captured on the same light path flowing back through focusing lens 407. Beam splitter 406 and discrete filter 410 are utilized to segregate the two signals before fluorescence signal 415 is directed to drum spectrometer 600. It should be recognized by those skilled in the art that the prism 208 may be advantageously combined as shown with fluorescence measurement cell 400 and reflectance cell 204. Prism 204 has no optical effect on the epifluorescence light paths but advantageously saves on having to add a separate window for the fluorescence measurement cell 400, among other advantages.

The physical configuration of drum spectrometer 600 is best illustrated with reference to FIG. 10. Drum 610 is attached at either end to shafts 611 and 614 and the shafts are rotatably positioned within bearings 612 and 613. Coupling 625 is connected to a motor or drive (not shown) and is further coupled to shaft 614, which in turn is fixed to drum 610. It should be appreciated by those skilled in the art that the drive may be controlled by a control device electrically coupled to the drive controlling movement of the drum and filter assemblies. Filter assemblies 604, 704, 803, 904, 1003, and 1103 are mounted within drum 610 as will be described more fully herein below.

Figure 9:
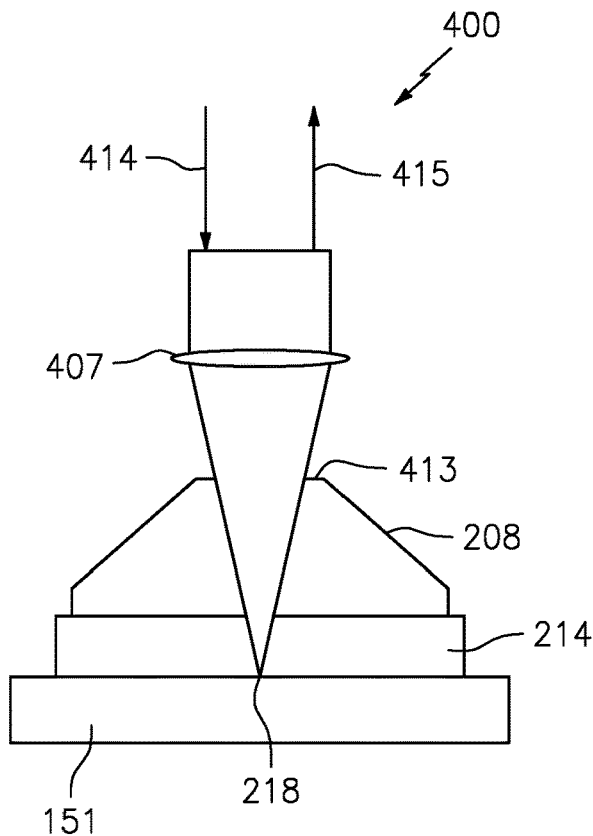
FIG. 9 is a schematic representation of fluorescence cell in accordance with certain aspects of the present disclosure.
Figure 10:
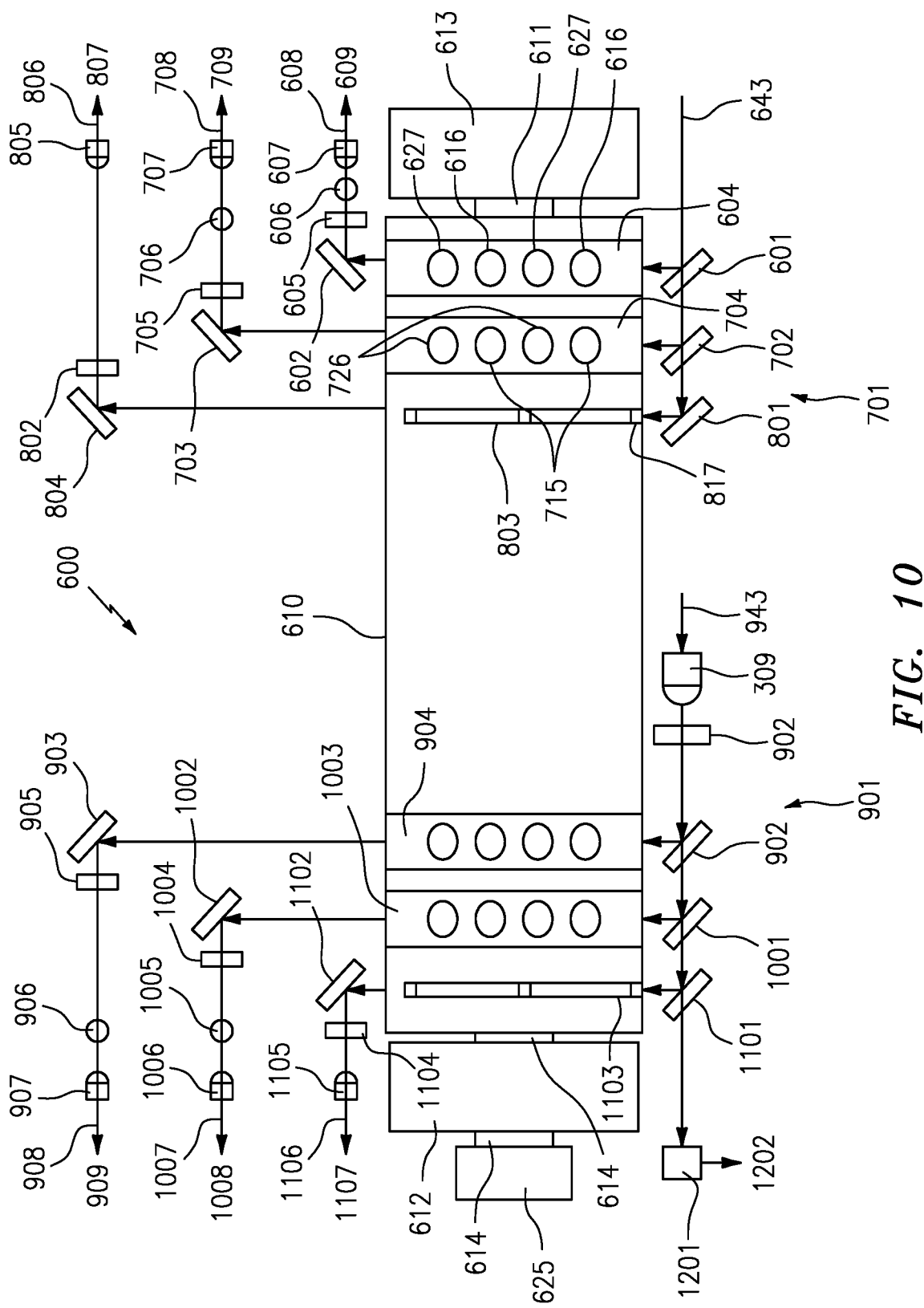
FIG. 10 is a top view of a drum spectrometer in accordance with certain aspects of the present disclosure.

Referring to FIG. 10, the first set of channels, the measurement channel set 701, direct light, depicted by light path 643, from reflectance cell 204 (FIG. 7), absorption cell 105 (FIG. 4), fluorescence measurement cell 400 (FIG. 9), and direct reference (light paths 1-4 of FIG. 3) to drum assembly 600. The light is directed into input ports 715 of discrete filter assembly 704 and input ports 616 of discrete filter assembly 604. It should be appreciated that there exists six pairs of input ports 615 and 616, radially positioned about drum 610, only two pairs of which can be seen in the figure. Behind each input port 615 and 616 are mounted the individual discrete filters as will be described herein below. In operation, light from light path 643 enters beam splitter 601 and filter 602 and is presented to the discrete filters of discrete filter assembly 604 through input ports 616. Light that matches any of the bandpass wavelengths of the discrete filters of assembly 604 as they are rotated past beam splitter 601 and filter 602 travels through the drum 610 and exits the drum through output ports 627 and is directed by mirror 605 toward detector 609. The operation of filter assembly 704 is the same as discrete filter assembly 604 except that the filtered light exits the drum through output ports 627 and is directed to mirror 705 and on to detector 709. Light path 643 is similarly passed to mirror 801 and filter 802 where it is directed through slot 817 behind which is mounted angle tuned filter assembly 803. The light is filtered at the various wavelengths described herein above as the incidence angle of light relative to the angle tuned filter assembly changes as drum 610 rotates. The filtered light exits the drum through an output slot (not shown) radially displaced from slot 817 and is directed by mirror 804 toward detector 807.

The second set of channels, parallel reference channels 901, direct light received from a broadband source 100 (FIG. 3), depicted by light path arrow 943 (light path 9 of FIG. 3), to drum assembly 600 into input ports behind which are drum filter sets 904 1003 and into input slot behind which is mounted angle tuned filter assembly 1103. The operation of parallel reference channels 901 is the same as that stated herein above with reference to the measurement channel set 701 albeit having different specific optical components and detectors. In addition, broadband light from beam splitter 902 is passed to an optical fiber (not shown) and is detected on lamp monitor detector 1202 to monitor the broadband source 100 (FIG. 3).

Figure 11:
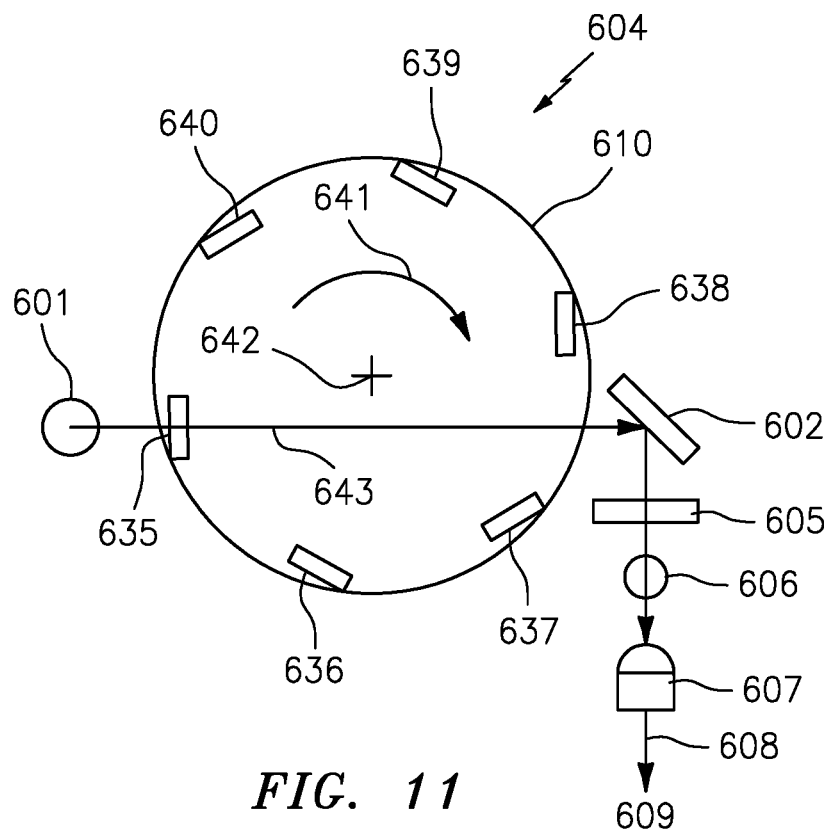
FIG. 11 is a schematic representation of a discrete filter assembly in accordance with certain aspects of the present disclosure.

Referring now to FIG. 11, there is shown a schematic representation of discrete filter assembly 604 mounted within drum 610. In the example shown, and as described herein above, discrete filter assembly 604 includes filter 635 having a band pass wavelength of 434 nm; filter 636 having a passband wavelength of 500 nm; filter 637 having a passband wavelength of 600 nm; filter 638 having a passband wavelength of 700 nm; filter 639 having a passband wavelength of 780 nm; and filter 640 having a passband wavelength of 850 nm all mounted within drum 610. Drum 610 is rotated in the direction shown by arrow 641 about the center of rotation 642. Discrete filters 635-640 are mounted within drum 610, approximately 60 degrees apart, and are positioned orthogonal to the light path depicted by arrow 643 as the drum is rotated. As can be appreciated by those skilled in the art, as drum 610 rotates, each of the six discrete filters 635-640 are positioned in light path 643 in turn. Light that is within the passband wavelength of the individual filter, to the extent that such wavelengths exist in the light path, is passed there through to mirror 605 and mirror 606 and onto detector 609 (FIG. 3). It should be further appreciated that positioning light path 643 outside (below in the example shown) of the rotational axis of drum 610, and positioning the filters at 60 degree angles relative to one another, allows for additional filters to be included in discrete filter assembly 604 than might otherwise be possible. It should further be appreciated that while the drum 610 rotates, there will be periods when no light from light path 643 passes through the drum, a "dark" period, and the detector 609 will not receive any light. For conciseness, discrete filter assemblies 704, 904, and 1003 of FIG. 10 have the same configuration as 604 depicted in FIG. 11.

Figure 12:
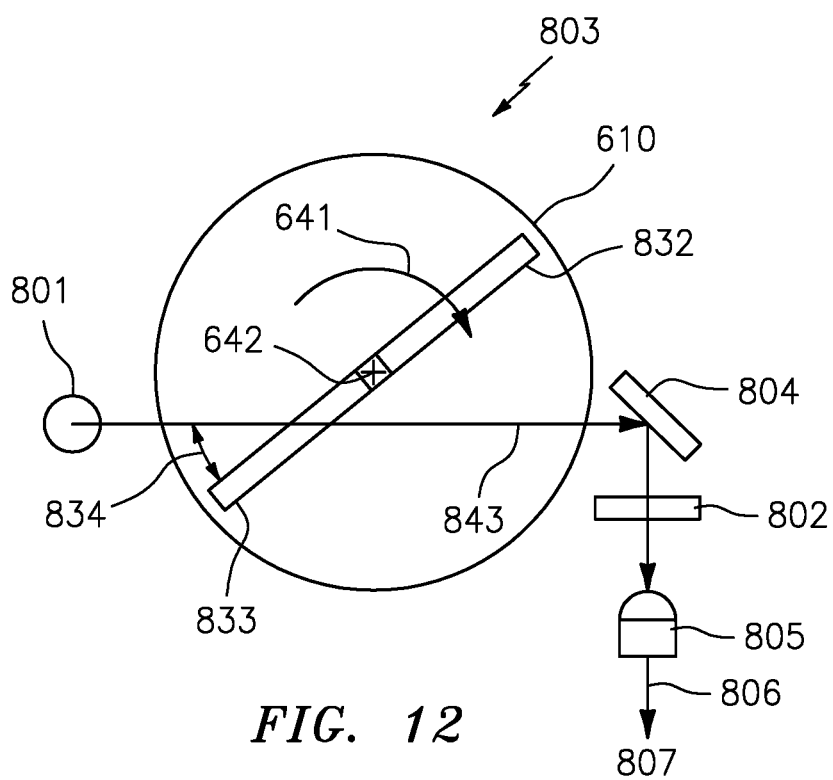
FIG. 12 is a schematic representation of an angle-tuned filter assembly in accordance with certain aspects of the present disclosure.

Referring now to FIG. 12, there is shown a schematic representation of adjustable filter assembly or angle tuned filter assembly 803 mounted within drum 610. In the example shown, and as described herein above, angle tuned filter pair 832 and 833 are mounted within drum 610. The drum 610 is rotated in the direction shown by arrow 641 about the center of rotation 642. The angle tuned filter pair 832 and 833, are positioned such that as the angle of incidence 834 changes wavelengths of light and are passed from mirror 801 and filter 802 through the angle tuned filter 833 at 4 nm spacing onto mirror 804 and directed to detector 807 (FIG. 3). It should be further appreciated that positioning light path 843 outside (below in the example shown) of the rotational axis of drum 610 allows for a full sweep of the pair of angle tuned filters 832 and 833. For conciseness, the angle tuned filter assembly 1103 of FIG. 10 has the exact same configuration as 803 depicted in FIG. 12.

Example Light and Signal Processing of an Optical Fluid Analyzer

Having described the light paths and associated components of OFA module 32 hereinabove, the processing steps that the signals are subject to in order to produce a meaningful spectrum will now be described with reference to FIG. 13 as well as FIG. 3. The photo-detectors 2001 of detector module 620 each produce an analogue signal 2002 that is proportional to the intensity of light incident on each respective detector. Analogue signal 2002 is amplified and filtered using any known method by amp/filter 2003 and is then routed to analogue-to-digital converter 2004 (ADC). The ADC sampling process 2005, as well as other processes described herein, may be controlled by software that may reside on processor 2000, for example, wherein the processor may be comprised of any known computing device and may further be comprised of more than one processors and may advantageously be located within formation wireline tester 20 and/or located at the surface such as processing unit 24 (FIG. 1). The ADCs 2004 simultaneously sample eight channels from detectors 609, 709, 807, 909, 1008, 1107, 1150, and 1202. The ADCs 2004 may also advantageously include an anti-aliasing digital filter stage.

The processor 2000 filters and sub-samples the signals within sub-sampling filter 2006 from all eight channels in order to further reduce the noise level and to reduce the sample rate down to any desired level. Simultaneously, an encoder 2008, which can comprise a rotary encoder, sends a signal to the processor indicating the angular position of the rotational portions of drum 610. In one embodiment of the present disclosure the encoder 2008 measures the angular position of the drum within a 90° quadrant to a resolution of about the equivalent of 0.02° of rotation. A timer (not shown) within the processor 2000 may be used to measure the duty cycle and an additional Hall sensor 2009 mounted within proximity of drum 610 is used to determine the quadrant that the drum is rotating through. The software within the processor 2000 continuously tracks the position of the rotation portions of drum 610 as it rotates with respect to time. In one embodiment of the present disclosure, the filters within drum 610 rotate at a predetermined rate of rotation such that the filters are positioned, with respect to the signals, at a preselected position. It should be appreciated that the rotational speed of the filters could be slowed, stopped, or reversed and restarted to take more data at any certain position of the rotation which would, among other advantages, increase the signal-to-noise ratio.

As each photo-detector ADC sample is taken, the sampled signal 2010 is labeled with the last reported drum position signal 2011 from the encoder 2008. In certain embodiments, the sampling rates of the drum position and photo-detector signals may not be the same and may not be time synchronized. In this case, the software on the processor 2000 includes drum position interpolation 2012 in order to calculate the drum position for each individual sample. The software may also buffer the samples and then calculates a more accurate rotational drum position using the sample time, the reported drum position and time, as well as the speed and acceleration of the rotational portion of the drum. In some embodiments, signal stream 2013 coming from the photo-detectors comprises eight channels of 32-bit samples, each tagged with the relative rotational drum position sampled at 2 kHz.

The software that reside within processor 2000 may contain the parameters, or profiles, of each of the optical filters mounted rotationally within the drum 610. It should be appreciated by those skilled in the art that this data includes the center wavelength, the bandwidth, and the angular position of each filter mounted within the drum, some or all of which may be temperature dependent. It should further be appreciated that certain aspects of these parameters may be temperature dependent and that steps must be taken to account for changes due to temperature. In the case of the angle-tuned filters 803 and 1103, the angle-tuned parameters 2018 also include a fitted curve that is used to determine the pass-band wavelength from the angular position of the filter relative to the incident light. The parallel reference signal 2015 associated with discrete filters 904 are compared with the parallel reference discrete filter parameter profiles 2016. The parallel reference signals 2017 associated with the angle-tuned filters 1103 are compared with the parallel reference angle-tuned filter parameter profiles 2018. The sample, or measurement, signals 2019 associated with discrete filters 604 are compared with the measurement discrete filter parameter profiles 2020. The sample signals 2021 associated with the angle-tuned filters 803 are compared with the measurement angle-tuned filter parameter profiles 2022. There are additional profiles 2023 used to mark points in the drum's rotation at which the signal can be considered to be dark to perform a dark measurement as will be disclosed in more detail herein below.

In operation, as the drum upon which the filters are mounted rotates, software on the processor 2000 determines which filter the light for each ADC channel is passing through and converts the drum angle into a wavelength. The processor then adds this wavelength information to the signal stream for assignment into its proper wavelength bin as will be more fully described herein after.

The software may also advantageously include a configurable set of wavelength bins, the reference wavelength bins 2024, and the sample signal wavelength bins 2025. These bins are comprised of a center wavelength (in nanometers) and a width (in nanometers) of the wavelength. These bins define the wavelengths that will be reported for each spectral measurement. The samples in the signal stream are assigned to one of these bins, depending on their tagged wavelength.

There may be multiple sample signals per wavelength bin 2025. As the sample signals are added to a particular bin, they are weighted using a configurable windowing function. The windowing function uses a higher weighting for sample signals having a center frequency close to the center of the frequency bin, and a lower weighting for sample signals having a center frequency close to the edge of the bin. For instance, the signals coming from the measurement discrete filter parameter profiles 2020 go through windowing function 2026 before being assigned to any particular bin within sample signal wavelength bins 2025.

Figure 13:
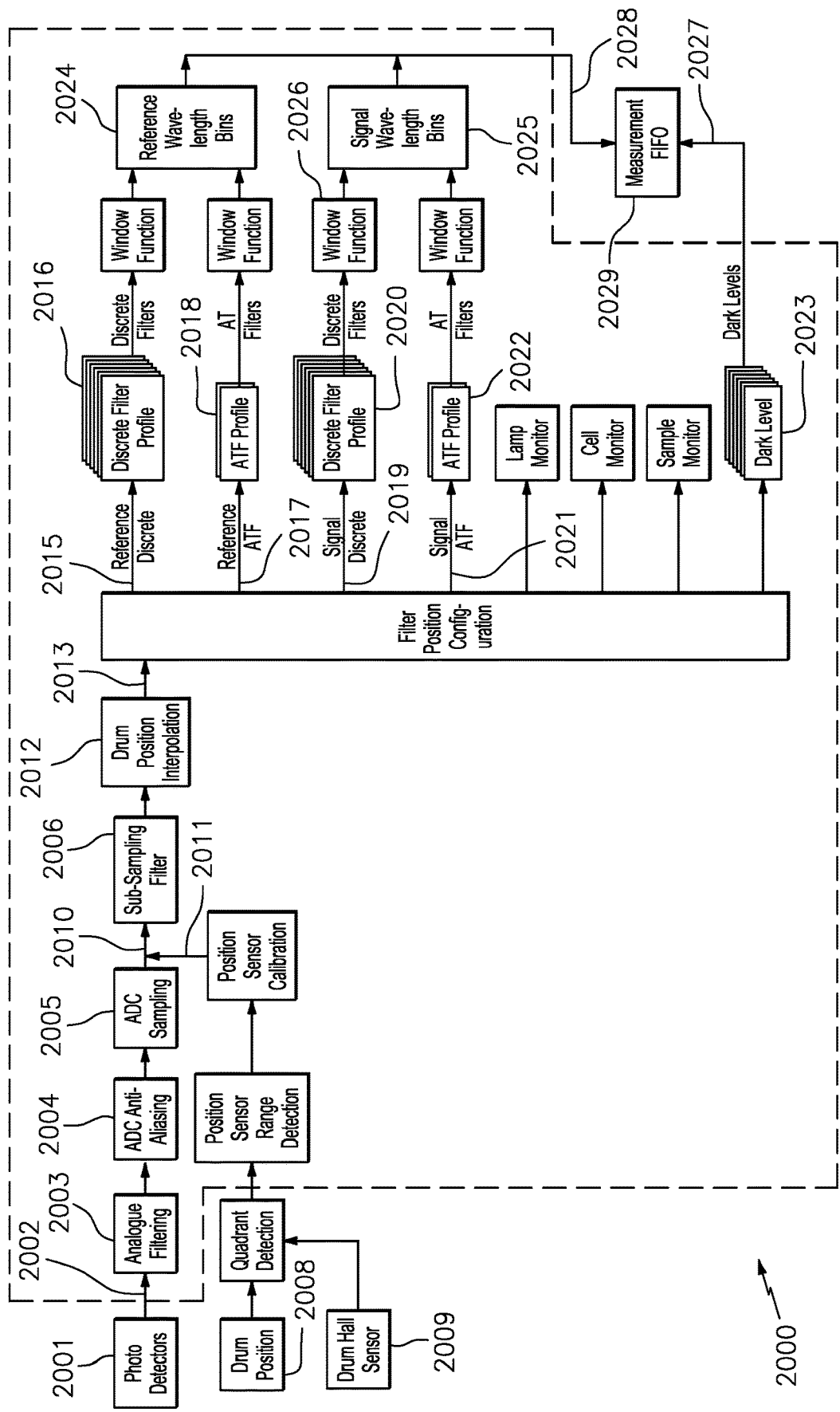
FIG. 13 is a flow chart of a control system in accordance with an embodiment of the present disclosure.

Still referring to FIG. 13, the measured dark levels 2027 are subtracted from the sample signals, and dependent on the measure type, the ratio between the individual sample signal and respective parallel reference stream is obtained. The resulting spectrum 2028 may be added to measurement first-in-first-out (FIFO) memory 2029, and may further be processed by processing unit 24 (FIG. 1).

The electrical control and operation of the present disclosure is now described with reference to the various figures. When the OFA module 32, or optics module, is powered on, software residing in the module runs a self-test script. The purpose of the self-test is to detect any faults prior to deployment of the tester in a well or in situ as necessary for confidence checking. The OFA module 32 then enters a stand-by mode while the tester is deployed to a first predetermined depth within a wellbore. Cooling may then be switched on if the sensors/detectors temperature reaches a pre-determined threshold during deployment within the wellbore. Prior to taking any measurements, cooling is provided to the detectors to facilitate the detectors reaching the lowest possible temperature while deployed. Once the detectors have reached a stable temperature, the OFA module is taken out of stand-by mode and completely powered up. In wells of relatively low temperature, the cooling may not be required and in other circumstances, less cooling may be used to free power for other purposes, consistent with adequate measurement quality at the time.

Measurements that can be made with the present disclosure, include, but are not limited to, fluorescence, phase, composition, absorption, reflectance, reference, and others. The measurements may be done in a predetermined sequence or ordered manually from the operator at the surface. Not all measurements need to be done at any of the predetermined testing locations. Once a particular measurement is made, for example a fluorescence measurement performed by the fluorescence measurement cell 400 (FIG. 9), the electrical output from detector 609, of the detector module 620, is converted to a digital signal proportional to the intensity of the light hitting the detector module 620. This signal is sent to a signal processing algorithm within a computing device. Processed or raw data can be sent to the processing unit 24 (FIG. 1) for further analysis. In certain embodiments, these signals may be sent to FIFO buffers (FIG. 13) and then sent for further analysis as described with reference to FIG. 10 directly herein above. The OFA module 32 continues to take measurements using other optics sensors (or repeating measurements if desired). The duration of the test depends on many factors including the type of test (fluorescence, reflectance, absorption, etc), the number of times the measurement is made, the type of data desired (running average versus single point), formation conditions and other factors. Once all of the desired measurements are made, the OFA returns to the 'ready' mode. Referring back to FIG. 1, the formation tester 20 is then positioned in another predetermined location and the sequence of measurements is repeated as desired. Once all of the measurements are made at all of the desired predetermined locations (depths) the OFA module 32 is powered down and the formation tester 20 may be brought to the surface.

Examples of Utilizing Tools for Monitoring, Analyzing and Characterizing Downhole Fluids The operational aspects of spectrometer assembly 600 (FIG. 10) with respect to providing downhole fluid property measurements, is best described with reference to FIG. 14. There is shown an example of the deconvolved theoretical output of a spectrometer of the present disclosure for certain fluids typically found in a downhole environment. The absorption spectrum shown is from light output from absorption cell 105 (FIG. 4) for various constituents and is displayed as optical density plotted against wavelength for both the visible range and the near infrared range. It should be appreciated by those skilled in the art that the raw output, before being deconvolved, of absorption cell 105 would be the sum of the optical density for all of the constituents in the mixture plotted against wavelength. The use of the present disclosure in the identification of individual constituents within the mixture will be described more fully herein below. In the example shown in FIG. 14, curve 920 is an example of a absorption spectrum for an oil-based mud with a decaying portion in the visible range and a peak somewhere around 1700 nm. Curve 921 represents the absorption spectrum for a first reservoir fluid and has various absorption features with corresponding optical densities shown in the 1700 nm range. Curve 922 represents the absorption spectrum for a second reservoir fluid and it also has various absorption features with corresponding optical densities shown in the 1700 nm range. It is known that different oils have variations in their molecular structure that cause them to have different colors and corresponding differences in absorption at the lower frequencies dues to electrical absorption. It is also known that most oils have a strong characteristic absorption peak at about 1725 nm due to molecular vibration absorption of the light because a typical carbon atom will have two hydrogen molecules attached thereto. Curve 923 represents the absorption spectrum for water with well-known significant peaks at 1445 nm and 1930 nm. Curve 924 represents an example of a absorption spectrum for $CO_2$ with a maximum peak at about 2013 nm and a trough at 2045 nm.

As described herein above, downhole spectrometers of the prior art typically comprise twenty or fewer channels. It is therefore virtually impossible to deconvolve and reproduce the entire spectrum of a fluid as shown in FIG. 14. Instead, spectrometers of the prior art comprise a discrete filter or channel having a bandpass wavelength along the spectrum corresponding to qualitative measures for identifying the presence (or absence) of a fluid of interest within the tester flow line. For instance, spectrometers of the prior art typically position a channel at about 1445 nm and 1930 nm to detect the presence (or absence) of a water peak and another channel at about 1725 nm to detect the presence or absence of oil. Because of the strong peaks and the wavelength separation between water and oil, these prior art spectrometers make it very easy to differentiate between the fraction of water and the fraction of oil in the tester flow line. For the reasons discussed herein above, spectrometers of the prior art lack the capability to provide better resolution at points along the spectrum to provide more information about the properties of the fluids in the flow line.

Figure 14:
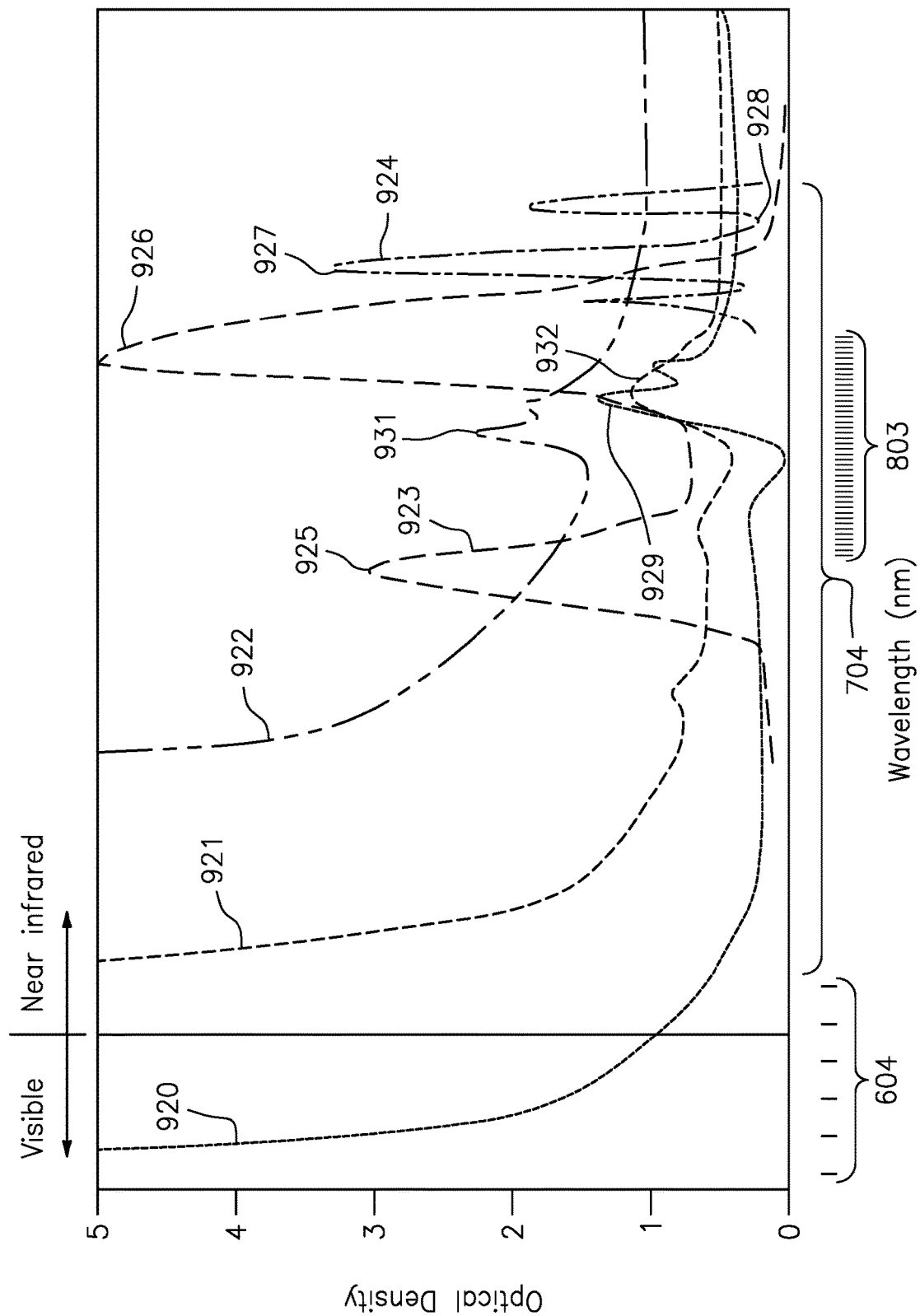
FIG. 14 is a graphical representation of the spectral output for various fluids of an optical fluid analyzer in accordance with certain aspects of the present disclosure.

Still referring to FIG. 14, the discrete filters of discrete filter assembly 604 are shown graphically with their approximate wavelength within the visible region and extending into the near infrared. The use of a drum spectrometer of the present disclosure allows for the positioning of six discrete filters, in one embodiment having wavelengths of 434 nm, 500 nm, 600 nm, 700 nm, 780 nm and 850 nm, within this area of interest to accurately detect the presence or absence of a fluid of interest at lower wavelengths. For example, many of the oil-based drilling muds are comprised of synthetic-type oils, which typically lack the aromatic components of naturally occurring hydrocarbons, and will have a higher absorption spectrum at lower wavelengths. The present disclosure has increased resolution at these lower wavelengths and may be useful to accurately monitor the presence of oil-based muds to determine, for example, when the flow line is free of filtrate to enable the taking of a clean sample of hydrocarbons. In addition, because oil-based muds may be recycled and blended, the present disclosure may be able to distinguish between different types of oil-based muds in a mixture and when used with multivariate analysis software, such as software offered by CAMO Software AS, be able to permit quantitative analysis of each in the mixture. In addition, as shown in FIG. 9, the fluorescence light source comprises a blue LED 401 having a wavelength between 457 nm and 463 nm. It should be appreciated by those skilled in the art that if the fluid in flow line 151 fluoresces, the relatively dense spacing of filters in this wavelength range provides a means of determining oil-based mud filtrate from reservoir hydrocarbons comprised of a light color.

The discrete filters of filter assembly 704 are also shown graphically in FIG. 14 with their approximate wavelength within a wide portion of the near infrared range. The use of a drum spectrometer of the present disclosure allows for the positioning of six discrete filters, in one embodiment having wavelengths of 935 nm, 1080 nm, 1290 nm, 1450 nm, 2013 nm and 2045 nm, within this area of interest to accurately detect the presence or absence of a fluid of interest at this wavelength range. For instance, the filters at wavelengths 935 nm and 1080 nm are important for detecting the presence of a first production fluid 921 at the lower near infrared wavelengths. The filter at 1290 nm is useful for detecting the presence of a second production fluid 922. The significance of being able to detect the compositional variations between two different production fluids is the ability to determine reservoir connectivity. The two different fluids most likely come from different non-connected compartments within the formation. This type of information is critical in designing the completion, determining economic reserves, and in production planning. The present disclosure enables the positioning of more filters within the near infrared wavelength region than spectrometers of the prior art and therefore enhances the ability to accurately determine compositional information about the fluids within the flow line.

Referring still to FIG. 14, and still with reference to discrete filter assembly 704, is the ability of the present disclosure to detect and quantify $H_2O$ present in flow line 151 (FIG. 4) as depicted by curve 923. As discussed herein above, $H_2O$ has a characteristic peak 925 at 1450 nm and a second, stronger, peak 926 centered at about 1930 nm. Discrete filter assembly 704 of the present disclosure may include a filter having a center bandwidth of 1450 nm as show in FIG. 14 to monitor characteristic peak 925, and may also, or alternatively, include a filter having a center bandwidth of 1930 nm to monitor for peak 926, both associated with the presence of water in flow line 151.

Also shown in FIG. 14, with reference to discrete filter assembly 704, is the ability of the present disclosure to detect and quantify $CO_2$ present in flow line 151 (FIG. 4) as depicted by curve 924. As discussed herein above, $CO_2$ has a characteristic absorption peak 927 at 2013 nm and a corresponding characteristic trough at 2045 nm. Because water has a peak at 1930 nm, an exemplary embodiment of discrete filter assembly 704 of the present disclosure includes both a filter at 2013 nm and at 2045 nm to confirm the presence of $CO_2$ in flow line 151, for example, in the presence of water-based muds. Heretofore, spectrometers have been of limited accuracy at low concentrations of $CO_2$ and especially so in the presence of water-based drilling fluids. As discussed herein before, the present disclosure enables the positioning of more filters within the near infrared wavelength region than spectrometers of the prior art and therefore enhances the ability to accurately quantify $CO_2$ within the flow line. Similar to connectivity, the ability to accurately quantify $CO_2$ directly influences the ability to determine reserves and perform production planning.

Still referring to FIG. 14, an embodiment of angle-tuned filter assembly 803 is depicted, and as described herein above, the filter assembly, comprises a pair of angled-tuned filters having a 4 nm increment between each measurement as the filters are rotated within drum assembly 600 (FIG. 10)

relative to stationary light directed therein. It should be appreciated by those skilled in the art, this particular embodiment of the present disclosure provides for 70 measurement increments between 1550 nm and 1830 nm, with a 10-15 nm spectral resolution, and that such a fine sampling interval yields a highly refined spectral resolution in the area of interest. In fact, with such a fine sampling interval, the curves presented in FIG. 14 within this region may be produced with great accuracy without much need for curve fitting techniques. In other words, angle-tuned filter assembly 803 not only reveals the vibrational peaks of the mixture of fluid components within the flow line, the output of the drum spectrometer 600 of the present disclosure can enable the ability to identify subtle differences between the fluids within the wavelength range of 1550 nm and 1830 nm and produce representative curves for each such fluid as will be described more fully herein below. It should be appreciated by those skilled in the art that the present disclosure may also enable the fingerprinting of fluids within the flow line, downhole and in real time. The present disclosure could not be realized utilizing discrete filters of the prior art because even if one could obtain such filters having center bandwidths at 4 nm spacing, it would be virtually impossible to install 70 such filters in a downhole tool.

Still referring to FIG. 14, and with special attention to the "oil window", or the wavelength range between 1550 nm and 1830 nm, an operational example of the present disclosure is disclosed. Oil-based mud 920 has a vibrational absorption peak at 1745 nm and has a distinctive shape throughout the oil window. First production fluid 921 has a vibrational absorption peak at 1760 nm and has its own distinctive shape throughout the oil window. Similarly, second production fluid 922 has a vibrational absorption peak at 1710 nm and has its own distinctive shape throughout the oil window. The ability to obtain such high spectral resolution within the oil window enables the fingerprinting of oil-based mud indicated by curve 920, first production fluid 921, and second production fluid 922. Although first production fluid 921 and second production fluid 922 are shown on the same spectrograph in FIG. 14, the fluids may not have been flowing in flow line 151 (FIG. 4) at the same time and may have been obtained at different downhole testing positions within the wellbore. The fingerprinting information may be stored and used at subsequent downhole testing positions to determine connectivity or compartmentalization of reserves. The fingerprinting information may also be used on subsequent wireline testing in the future to determine changes in the reservoir such as gas to oil ratio (GOR), water fraction, etc, and further assist in production planning such as enhanced oil recovery (EOR) actions. In addition, such fingerprinting information is useful, for example, in determining EOR incremental recovery, and can used in conjunction with the sigma-derived values of downhole fluids as described in co-pending application number WO2017015340, the disclosure of which is incorporated by reference herein in its entirety.

Figure 15:
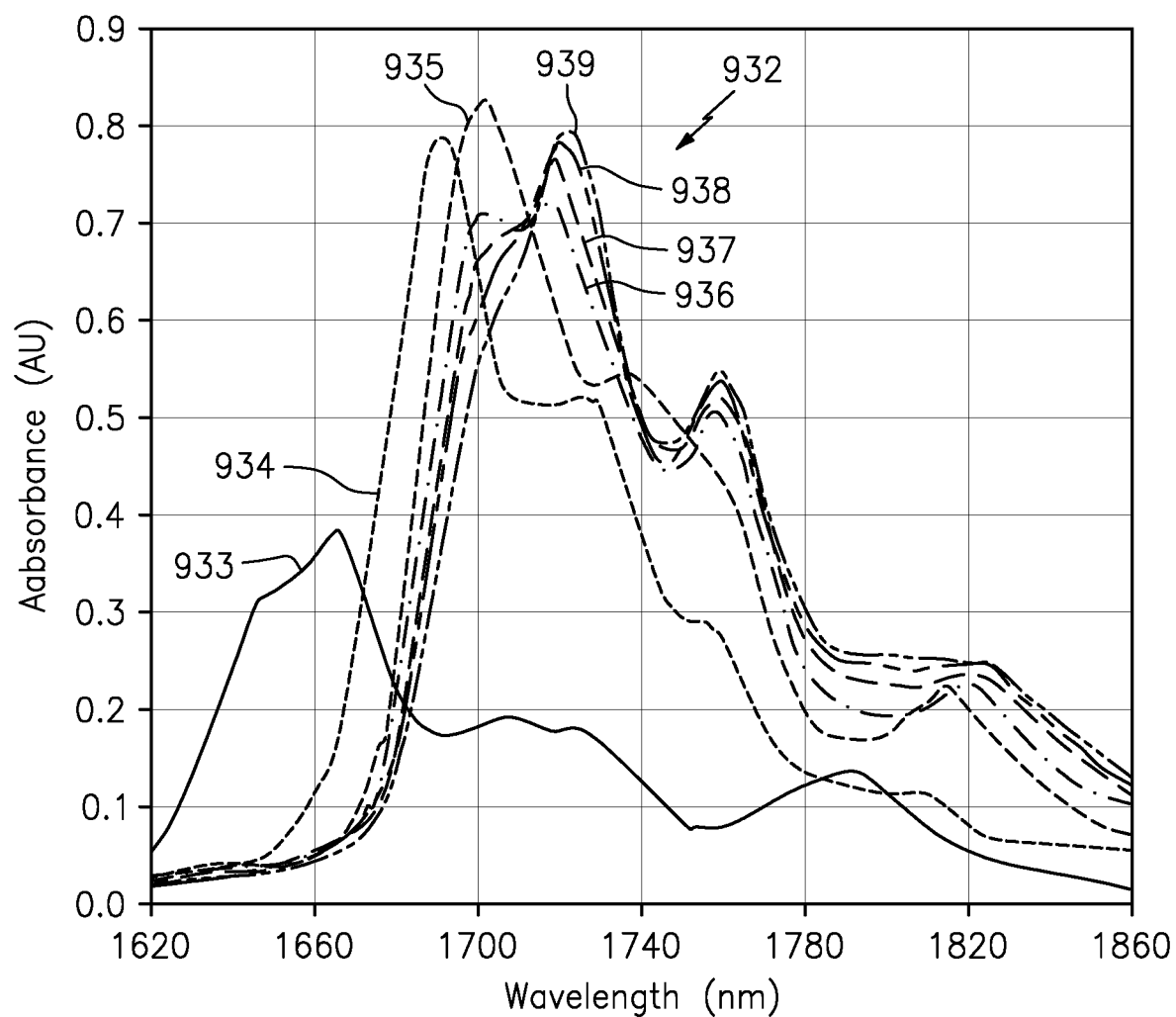
FIG. 15 is a graphical representation of an example of spectral output for pure hydrocarbons.

The spectral analysis of the high resolution spectral output of optical fluid analyzer in the oil window of the present disclosure may provide downhole quantitative analysis of a mixture of well fluids utilizing correlations between component partial densities and the spectra. Utilizing a calibration data set based on spectra data for, as an example, pure hydrocarbons $C_1$-$C_7$, at least in the hydrocarbon window of wavelengths, as well as mixtures thereof, regression coefficients can be determined for use in various correlation techniques. An example of such a data set 932 is shown graphically for pure hydrocarbons $C_1$-$C_7$, 934-939 respectively, in FIG. 15 within the wavelength range of 1620 nm to 1860 nm. As described herein above with reference to FIG. 14, the optical fluid analyzer of the present disclosure would provide at least 53 measurements in this wavelength range. Various methods may be used for correlating, or deconvolving, the output spectra with the data sets to provide downhole identification and quantitative analysis of the well fluids. Such known techniques include principal component analysis (PCA), principal component regression (PCR), partial least squares regression (PLSR), and least squares estimation (LS), among others. In the field of quantitative chemometrics, PLSR is sometimes preferred because of the way it handles unknowns mixed in with a particular fluid of interest, or target analyte. In the case of using PCA, such technique is based on singular value decomposition, and is useful to determine the number of non-zero singular values, and thus how many unknowns can be independently estimated. Using such techniques, and combinations thereof, it may possible with the present disclosure to quantify the amount of a particular fluid of interest within a mixture of well fluids downhole and in real time.

Figure 16:
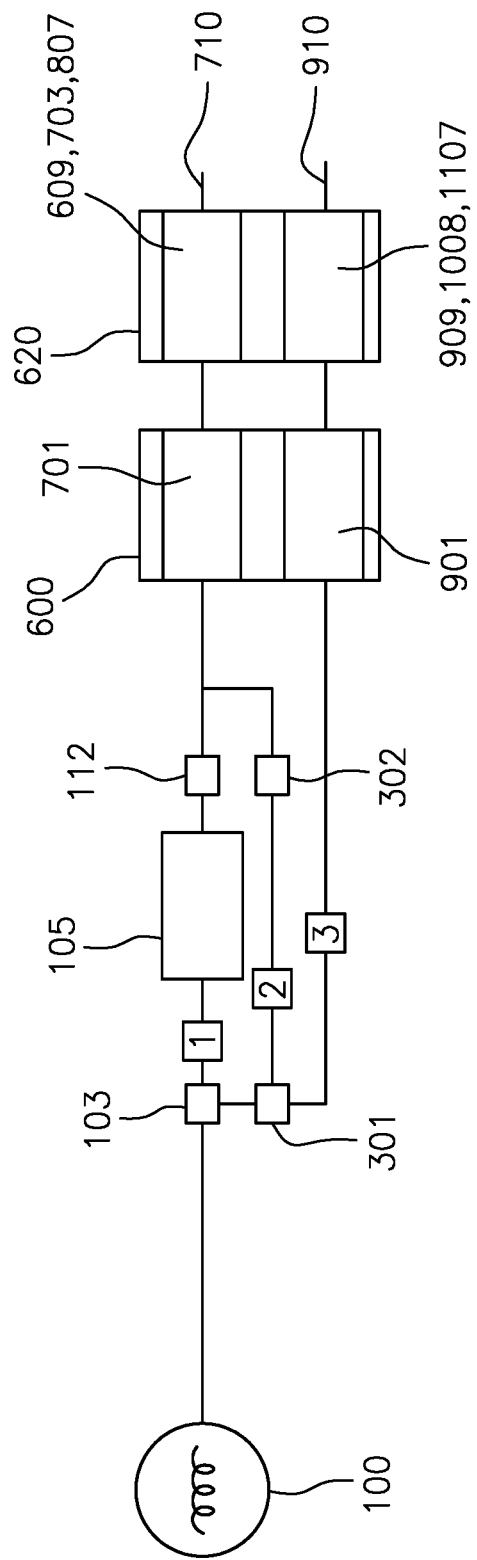
FIG. 16 is a schematic representation of the light paths for various optical components of an optical fluid analyzer in accordance with certain aspects of the present disclosure.

The optical analyzer of the present disclosure is unique in that it provides a parallel reference signal and a direct reference signal. It is an important aspect of the present disclosure that, unlike prior art optical fluid analyzers, the direct reference signal completely bypasses the testing cell of the analyser. Referring to FIG. 16, the reference signal aspects of the present disclosure will be described using a simplified version of absorption cell light path 1, direct reference light path 3 and parallel reference light path 9 of FIG. 3. As described herein above, broadband light from source 100 is exposed to downhole fluid in absorption cell 105 and a spectrum is produced using the filters in channel set 701 and the output 710 from detectors 609, 700, and 807. This measurement output is produced with shutter 112 in the open position and shutter 302 in the closed position. In one embodiment of the present disclosure, the optical analyzer is operated in a direct reference mode wherein shutter 112 is closed and shutter 302 is open. In direct reference mode, light from source 100 is directed through beam splitters 103 and 301 into light path 3 and into channel set 701 and detectors 609, 700, and 807 and the output signal 710 is a pure direct reference signal. The measurement signal output and the direct reference output signal are produced from the same set of filters and detectors and processed through the same analog to digital converters under the same conditions (pressure and temperature) at approximately the same time. The intensity of the light of the measurement signal output is compared to the intensity of the light from the direct reference signal output. In some embodiments, a measurement is made during one rotation of the measurement filter sets 701 and a direct reference is made during a subsequent rotation. It should be appreciated by those skilled in the art that by comparing these two reference signal outputs, the time dependent differences as well as the difference between detectors can be normalized as will be described herein below. Still referring to FIG. 16, the parallel reference aspects of the present disclosure are explained. As described herein above, the filters of channel set 701 and 901 are selected to be as close to identical as possible as are the detector pairs of detector module 620. In addition to pressure and temperature effects on the optical components that comprise a downhole analyzer, which may be changing relatively slowly, other factors may exist that change more rapidly that may produce deleterious effects on the accuracy of the output of such analyzers. One such factor is the temporal changes, or flickering, in source 100. In one embodiment of the present disclosure, with shutter 112 closed and shutter 302 open, the output 710 is the direct reference signal and this may be compared to the parallel reference output 910 at the same time. In doing so, the spectral intensity differences caused by temporal changes in the source 100 can be normalized as will be described more fully herein below. It should be further appreciated that with shutter 112 open and shutter 302 closed, the output 710 is a measurement output, or spectrum, and that output may be compared to parallel reference output signal 910. As discussed, the output made during a dark measurement period is indicative the noise of the detector. The normalization of the measurement signal by using the parallel and direct reference signals can be accomplished using the following relationship:

$$meas\lambda_{corr}(t') = \frac{(meas\lambda(t') - dark_1)}{(pref\lambda(t') - dark_2)} \times \frac{(pref\lambda(t'') - dark_2)}{(meas\lambda(t'') - dark_1)} \quad \text{(Equation 1)}$$

Wherein:
$meas\lambda_{corr}(t')$ is the corrected measurement output at wavelength $\lambda$, at time equals t';
$meas\lambda(t')$ is the raw measurement output at wavelength $\lambda$ produced at 710 at time equals t';
$dark_1$ is the averaged detector output produced at 710 during dark periods;
$pref\lambda(t')$ is the parallel reference output at wavelength $\lambda$ produced at 910 at time equals t';
$dark_2$ is the averaged detector output produced at 910 during dark periods;
$pref\lambda(t'')$ is the parallel reference output at wavelength $\lambda$ produced at 910 at time equals t"; and
$meas\lambda(t'')$ is raw measurement at wavelength $\lambda$ produced via the direct path at 710 at time equals t".
Time t" is preferably close enough to time t' that the apparatus temperature is similar.
The normalization of the measurement signal of optical fluid analyzer of the present disclosure may be shown by examples utilizing Equation 1 with reference to Table 1. For convenience, the dark signals are taken as zero without altering the generality of Equation 1, and the source intensity is taken as constant with time.
The cell contents in this example absorb 50% at the two wavelengths but the source intensity differs at these wavelengths. The parallel detector at wavelength $\lambda_2$ has 92% of the sensitivity of the detector at wavelength $\lambda_1$, due to manufacturing variation.
When the data in Table 1 is inserted into Equation 1, the corrected readings at each wavelength are 0.5, corresponding to the cell absorption of 50%. This example shows how both the spectral variation in the source, and detector variations can be compensated.

TABLE 1

| Wavelength | | $\lambda_1$ | $\lambda_2$ |
|---|---|---|---|
| Source Intensity | | 1.0 | 0.9 |
| Cell absorption factor | | 50% | 50% |
| Cell output Intensity | | 0.5 | 0.45 |
| Measurement Signal at 710 | $meas\lambda(t')$ | 0.5 | 0.45 |
| Reference Signal at 910 | $pref\lambda(t')$ | 1.0 | 0.9*0.92 = 0.83 |
| Reference Signal at 710 | $meas\lambda(t'')$ | 1.0 | 0.9 |
| Reference Signal at 910 | $pref\lambda(t'')$ | 1.0 | 0.9*0.92 = 0.83 |

$$meas\lambda_{1corr}(t') = \frac{(0.5 - 0)}{(1 - 0)} \times \frac{(1 - 0)}{(1 - 0)} = 0.5 \quad \text{(Equation 1)}$$

$$meas\lambda_{2corr}(t') = \frac{(0.45 - 0)}{(0.83 - 0)} \times \frac{(0.83 - 0)}{(0.9 - 0)} = 0.5 \quad \text{(Equation 1)}$$

While the foregoing description of the reference channels is relative to the absorption cell 105 (FIG. 4), it should be appreciated that signal output from the reflectance cell 204 (FIG. 7) can be similarly normalized using the techniques described herein above.

While the foregoing is directed to only certain embodiments of the present disclosure, certain observations of the breadth of the present disclosure should be made. Wireline, as referred to herein, may be electric wireline including telemetry and power. Wireline may also include wired slickline and wired coil tubing. Embodiments of the present disclosure include pumped-down-the-drill-pipe formation testing where the tools described herein exit through the drill bit. Otherwise heretofore conventional logging while drilling (LWD) that include the present disclosure allow for formation testing and sampling where the drill pipe may be wired for power and telemetry or some other telemetry such as mud pulse or electromagnetic through the earth. Further, commands and data can be stored using battery power, and power can come from a turbine during circulation.

In addition, while the foregoing is directed to only certain embodiments of the present disclosure, it should be appreciated by those skilled in the art that the present disclosure is not limited to any particular embodiment or field of endeavor. Other and further embodiments of the disclosure may be devised without departing from the basic scope thereof, and the scope thereof is determined by the claims that follow.

What is claimed is:

1. An apparatus for fluid analysis, comprising:
   a broadband source configured to produce a broadband light across a spectrum of wavelengths;
   a source splitter optically coupled to the broadband source and splitting the broadband light into a parallel reference channel and a measurement channel;
   the measurement channel including a test cell wherein the broadband light of the measurement channel is configured to interact with a fluid sample in the test cell;
   at least one adjustable filter assembly having a plurality of filters mounted thereon, the plurality of filters including a parallel reference set of filters configured to filter the parallel reference channel and a measurement set of filters configured to filter the measurement channel;
   at least one drive operable to move the at least one adjustable filter assembly; and
   a detection unit comprising a parallel reference set of detectors detecting the parallel reference channel after filtering with the parallel reference set of filters and a measurement set of detectors detecting the measurement channel after filtering with the measurement set of filters.

2. The apparatus of claim 1, wherein the plurality of filters comprise any of discrete filters, linear variable filters and angle tuned filters.

3. The apparatus of claim 2, wherein the at least one adjustable filter assembly comprises a plurality of preselected positions wherein the parallel reference channel and the measurement channel are concurrently filtered at the preselected positions.

4. The apparatus of claim 1, wherein the parallel reference channel includes a beam splitter optically connected to the parallel reference channel splitting the broadband light of the parallel reference channel into a direct reference signal, a pair of shutters having at least one selective orientation configured to block the measurement channel and to permit the direct reference signal to pass to a direct reference channel and on to the measurement set of detectors.

5. The apparatus of claim 4, wherein the direct reference channel bypasses the test cell.

6. The apparatus of claim 1, wherein the test cell comprises any of an absorption cell, a fluorescence cell and a reflectance cell.

7. The apparatus of claim 1, wherein the at least one adjustable filter assembly comprises a drum and the plurality of filters are mounted to an inside surface of the drum.

8. A method for performing fluid analysis, comprising:
generating a broadband light;
splitting the broadband light signal into a parallel reference channel and a measurement channel;
interacting the broadband light signal of the measurement channel with a fluid sample in a test cell;
filtering the broadband light signal from the measurement channel after interacting with the fluid sample through a measurement set of filters and filtering the broadband light signal of the parallel reference channel through a parallel reference set of filters; and
detecting the measurement channel after filtering with the measurement set of filters using a measurement set of detectors to produce a measurement output and further detecting the parallel reference channel after filtering with the parallel reference set of filters using a parallel reference set of detectors to produce a parallel reference output signal.

9. The method of claim 8, wherein the filtering of the broadband light from the measurement channel after interacting with the fluid sample through a measurement set of filters and the filtering the broadband light of the parallel reference channel through a parallel reference set of filters are performed concurrently.

10. The method of claim 8, further including correcting the measurement output using the parallel reference output signal and producing a corrected measurement output.

11. The method of claim 10, further including calculating at least one property of the fluid sample using the corrected measurement output.

12. The method of claim 10, further including producing at least a portion of an optical density spectrum from a plurality of the corrected measurement outputs.

13. The method of claim 8, wherein the test cell comprises an absorption cell, determining a direct reference signal and determining an amount of the broadband light that is absorbed within the fluid sample.

14. The method of claim 8, wherein the test cell comprises a reflectance cell, utilizing the measurement output and determining an incidence angle to detect any of a presence of gas, a presence of condensate, a presence of rich gas, a presence of lean gas, a presence of water, or a gas to oil ratio, in the fluid sample.

15. The method of claim 8, wherein the test cell comprises a fluorescence cell, utilizing the measurement output and determining a fluorescence signal and further detecting a bubble point or a phase of the fluid sample.

16. An optical fluid analyzer comprising:
a broadband light source;
an optical chassis comprising:
a flowline configured to include a fluid sample flowing therethrough;
an absorption cell optically coupled with the flowline; and
a prism assembly optically coupled with the flowline and comprising any of a reflectance cell and a fluorescence measurement cell;
a drum spectrometer assembly comprising a measurement filter assembly and a parallel reference filter assembly;
an absorption cell light path optically coupled to the broadband light source, the absorption cell and the measurement filter assembly;
a light path directed at fluid reflectance optically coupled to the broadband light source, the prism assembly and the measurement filter assembly;
a direct reference light path optically coupled to the broadband light source and the measurement filter assembly;
a fluorescence light path optically coupled to an fluorescence light source, the prism assembly and the measurement filter assembly;
a parallel reference light path optically coupled to the broadband light source and the parallel reference filter assembly;
a cell monitoring light path optically coupled to the absorption cell light path and to a cell monitoring light path detector;
a first discrete filter assembly disposed in the measurement filter assembly and optically coupled to a first detector;
a second discrete filter assembly disposed in the measurement filter assembly and optically coupled to a second detector;
a first angle tuned filter assembly disposed in the measurement filter assembly and optically coupled to a third detector;
a third discrete filter assembly disposed in the measurement filter assembly and optically coupled to a fourth detector;
a fourth discrete filter assembly disposed in the measurement filter assembly and optically coupled to a fifth detector; and
a second angle tuned filter assembly disposed in the measurement filter assembly and optically coupled to a sixth detector.

17. The optical fluid analyzer of claim 16 further comprising:
the first discrete filter assembly and the third discrete filter assembly are comprised of a matching first set of a plurality of discrete filters configured to filter any of the fluorescence light source and the broadband light source after interacting with the fluid sample to pass light in a visible range and a near infrared range;
the second discrete filter assembly the fourth discrete filter assembly are comprised of a matching second set of a plurality of discrete filters configured to filter the broadband light source after interacting with the fluid sample to pass light in the near infrared range; and
the first angle tuned filter assembly and the second angle tuned filter assembly are comprised of a matching a first angle tuned filter and a matching second angle tuned filer and configured to filter the broadband light source after interacting with the fluid sample to pass light in the near infrared range.

18. The optical fluid analyzer of claim 17 further comprising:

wherein the matching first set of a plurality of discrete filters are configured to filter any of the fluorescence light source and the broadband light source after interacting with the fluid sample concurrently;

wherein the matching second set of a plurality of discrete filters are configured to filter the broadband light source after interacting with the fluid sample concurrently; and wherein the matching a first angle tuned filter and a matching second angle tuned filer are configured to filter the broadband light source after interacting with the fluid sample concurrently.

19. The optical fluid analyzer of claim 18, wherein:

the first detector is configured to produce a first measurement output;

the second detector is configured to produce output a second measurement output;

the third detector is configured to produce output a third measurement output;

the fourth detector is configured to produce output a fourth parallel reference output signal;

the fifth detector is configured to produce output a fifth parallel reference output signal;

the sixth detector is configured to produce output a sixth parallel reference output signal; and the optical fluid analyzer further configured to produce a first corrected measurement output using the first measurement output and the fourth parallel reference output signal, to produce a second corrected measurement output using the second measurement output and the fifth parallel reference output signal, and to produce a third corrected measurement output using the third measurement output and the sixth parallel reference output signal.

20. The optical fluid analyzer of claim 16 further comprising:

the cell monitoring light path detector configured to produce a continuous signal indicative of a gross intensity of the broadband light source transmitted through the absorption cell after interacting with the fluid sample.

* * * * *